United States Patent [19]

Jones et al.

[11] Patent Number: 4,904,603

[45] Date of Patent: Feb. 27, 1990

[54] MONITORING DRILLING MUD

[75] Inventors: Timothy G. J. Jones, Waterbeach; Trevor L. Hughes, Chesterton, both of England

[73] Assignee: Schlumberger Technology Corporation, Houston, Tex.

[21] Appl. No.: 165,069

[22] Filed: Mar. 7, 1988

[30] Foreign Application Priority Data

Mar. 9, 1987 [GB] United Kingdom ............... 8705502

[51] Int. Cl.$^4$ ..................... G01N 33/24; E21B 49/08
[52] U.S. Cl. ....................................... 436/25; 436/27; 436/30; 436/31; 436/55; 436/161; 210/660; 210/669; 210/681; 73/153; 166/250; 175/42; 175/66
[58] Field of Search .................... 436/25, 27, 28, 30, 436/31, 56, 161, 55; 210/660, 662, 669, 681, 683, 685; 73/151-153; 166/250; 175/40, 42, 66

[56] References Cited

U.S. PATENT DOCUMENTS

| | | | |
|---|---|---|---|
| 2,772,951 | 12/1956 | Bond | 436/31 X |
| 4,306,879 | 12/1981 | Allen et al. | 436/30 |
| 4,385,666 | 5/1983 | Mamadzhanov | 175/40 |
| 4,447,340 | 5/1984 | Féry | 175/42 X |
| 4,472,354 | 9/1984 | Passell et al. | 422/62 |
| 4,495,800 | 1/1985 | Wilcox | 73/61.4 |
| 4,507,210 | 3/1985 | Lauzon | 252/8.5 A |
| 4,546,252 | 10/1985 | Dion | 250/252.1 |
| 4,635,735 | 1/1987 | Crownover | 175/48 |
| 4,807,469 | 2/1989 | Hall | 436/27 X |

FOREIGN PATENT DOCUMENTS 2498332 1/1981 France .
2066951 7/1981 United Kingdom .

OTHER PUBLICATIONS

Peterson et al., "Anal. Chim. Acta.", 1984, pp. 263-266.

Primary Examiner—Barry S. Richman
Assistant Examiner—Rebekah A. Griffith
Attorney, Agent, or Firm—Stephen L. Borst; John J. Ryberg

[57] ABSTRACT

The invention in one aspect provides a method of testing drilling mud in use which comprises periodically sampling the circulating mud and analyzing its aqueous filtrate at the rig site by ion chromatography for selected positive and negative ions; one or more other parameters of the sampled mud and/or mud filtrate (e.g. pH, temperature) may also be measured; preferably the composition of the mud filtrate thus monitored is interpreted to indicate downhole interactions, with the composition of the mud supplied to the hole being adjusted to or towards the optimum as drilling proceeds. The invention also provides a method in which the solids of the periodically sampled mud are analyzed at the rig site, e.g. for sorbed ions and/or for cation exchange capacity; the values so obtained are preferably combined with those for the mud filtrate analysis and used in the diagnosis of downhole conditions for adjustment of the composition of freshly supplied mud. The invention further provides a method of analyzing drilled shale solids in drilling mud in use which comprises drying and separating these solids from the mud, extracting ions from the separated solids into solution, and analyzing the resulting solution by ion chromatography for selected positive and negative ions; these operations are conducted at the rig site, and the resultant data, usually along with analyses of the circulating mud composition, are preferably used to indicate appropriate adjustment of the composition of the mud supply to or towards the optimum as drilling proceeds.

32 Claims, 25 Drawing Sheets

FIG.3
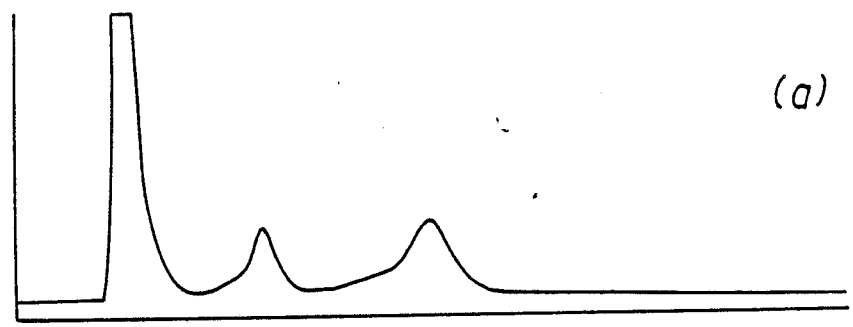
(a)
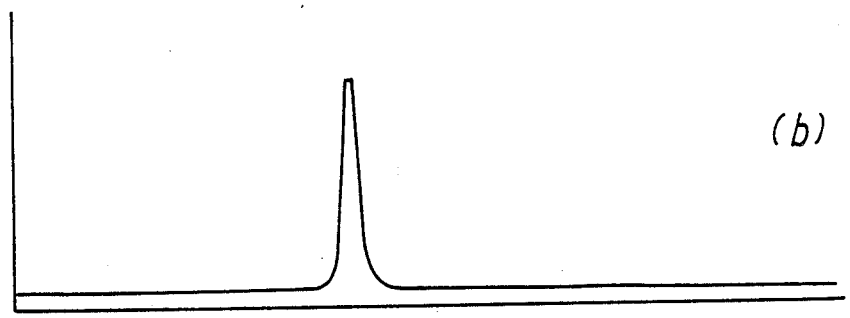
(b)
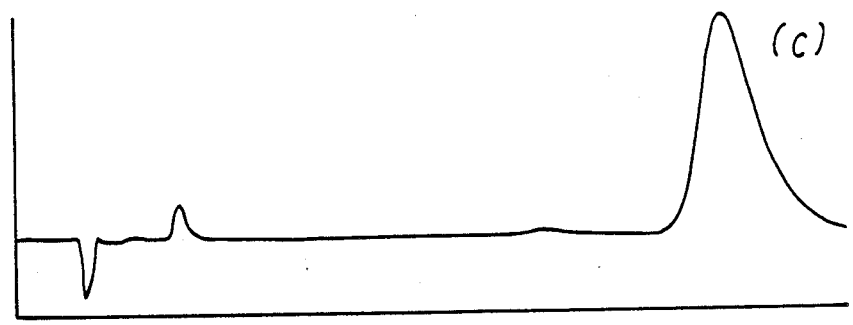
(c)

FIG.4

| DATE TIME | $c_i^m$ | | | | | | | pH | | T | $d_m$ | $d_a$ | $v_s$ | $t_{lag}$ |
|---|---|---|---|---|---|---|---|---|---|---|---|---|---|---|
| | Na | K | Mg | Ca | Cl | SO$_4$ | | m | f | | | | | |

FIG.6

| DATE TIME | CEC | $v_s$ | $d_s$ | $\bar{x}_i$ | $c_i^{ms}$ | $\Delta c_{ms}$ |
|---|---|---|---|---|---|---|
| | | | | | | |

FIG.7

| DATE TIME | $\bar{w}_a$ | $\bar{m}_j$ ||||| CEC | A | $z$ | $t_{lag}$ |
| | | Na | K | Mg | Ca | Cl | | | | |
|---|---|---|---|---|---|---|---|---|---|---|
| | | | | | | | | | | |

MONITORING DRILLING MUD

"Portions of this patent are related to U.S. Pat. No. 4,801,469 entitled "Monitoring Drilling Mud Circulation" which was filed on the same date and assigned to the same assignee."

The invention relates to a method of monitoring drilling operations and more particularly, drilling fluid, called drilling mud, and the cuttings to identify changes in the drilling process by continuously monitoring changes in the chemical composition of the mud. In a preferred embodiment, the invention relates to the use of ion chromatography at the rig site during drilling operations to analyze the ionic composition of drilling muds (filtrate and/or solids) and/or drilled solids (cuttings). The method is intended for use with both water-base muds and invert emulsion muds, although in the case of the latter usually the aqueous phase only is analyzed.

In the rotary drilling of wells, such as hydrocarbon wells, a mud is continuously circulated from the surface down to the bottom of the hole being drilled and back to the surface again. The mud has several functions, one of them being to transport the cuttings drilled by the drill bit up to the surface where they are separated from the mud. Another function is to impose an hydrostatic pressure on the walls of the borehole so as to avoid a collapse of the borehole and an influx of gas or liquid from the formations being drilled. The characteristics of the mud are therefore important to monitor and to keep within certain limits. For example, the density must be large enough so as to exert a certain hydrostatic pressure on the formations but not too large to fracture these formations. The viscosity of the mud is also an important characteristic since it contributes to the cuttings transport capability of the mud. Weighting materials, barite for example, are added to the mud to make it exert as much pressure as needed to contain the formation pressures. Clay is added to the mud so as to keep the bit cuttings in suspension as they move up the hole. The clay also sheathes the wall of the hole. This thin layer of clay, called wall cake, makes the hole stable so it will not cave in or slough. Numerous chemicals are available to give the mud the exact properties it needs to make it as easy as possible to drill the hole.

Maintaining the stability of the borehole is one of the major problems encountered in drilling oil and gas wells. It has been observed in the field that boreholes in shale sections frequently go out of gauge, losing material from the borehole wall. This material can become detached from the wall in the form of large fragments (cavings), which may be removed by the upward circulating mud, just as the drilled cuttings are. If the hole-cleaning capacity of the mud is insufficient, cavings collect on ledges and may cause the drill pipe to stick on pulling out of the hole. The necessity to re-drill through fill accumulated on the bottom of the hole during trips is another result of this process. In all cases there is a gradual build up of dispersed particles in the mud, too fine to be removed by the solids control equipment. This may give rise to a host of secondary problems: the increased solids content slows down the drilling rate and, as drilled solids form a poor filter cake, problems in controlling the fluid loss may cause differential sticking in permeable sands. Difficulty controlling the mud weight leading to lost circulation, and an unstable rheology are further problems of this kind.

In some circumstances, shales swell in contact with the mud in such a way that the wellbore diameter decreases. In such cases, identified in the field by a need for frequent reaming, the wellbore closes down on to the drill string, and there is once again an increased risk of sticking.

The various forms of hole instability resulting from the interaction between the drilling fluid and the subterranean formations penetrated by the borehole are related to the hydration and dispersion of the clay sediments.

During the drilling process, the ionic composition of the drilling mud changes from its original formulation. These changes in composition are in part a measure of the downhole processes which may be termed mud-rock interactions. An important example of mud-rock interactions is ion exchange between cations in the mud and in shale formations. In current drilling practice, the ionic composition of the mud is not monitored so that the extent of these interactions cannot be determined and the composition of the drilling mud cannot be accurately maintained.

One exception is the monitoring of the level of potassium ions in drilling muds at the rig site. Potassium salts are commonly added to muds to form inhibitive water-base drilling fluids to stabilize shale sections by a process which is presumed to be cation exchange. It is therefore recognized that potassium ions are depleted from the mud during the drilling of shale sections. The method recommended by the American Petroleum Institute (API RP 13B, 1980) for potassium analysis involves measuring the height of a centrifuged sediment obtained by the precipitation of the potassium from the filtrate as potassium perchlorate. In another method, potassium is precipitated using a known excess of sodium tetraphenylboron; the sodium salt remaining after the potassium salt is precipitated is then determined by titration with a quaternary ammonium salt. U.S. Pat. No. 4,546,252 describes a method of potassium determination based on measuring the concentration of the naturally-occurring radioactive $K^{40}$ isotope using a gamma-radiation detector.

The above methods probably give an adequate measure of the concentration of potassium ions in the mud system. However there is no comparable information on the concentration of other ionic species in the mud system. It will not generally be possible to interpret downhole processes based on the changes in the concentration of only one ion. Further, other cations such as calcium can be used to form inhibitive mud systems, and their level in the mud system should be maintained. In addition, the level of toxic chemicals from mud systems which are discharged into the environment should be controlled; however discharge concentrations are not accurately known.

In U.S. Pat. No. 4,507,210 a process is disclosed of formulating an aqueous drilling mud to minimize the swelling and dispersion of subterranean formations contacted by the mud. This process is based on a filtration method.

In U.S. Pat. No. 4,306,879, a log is prepared by analyzing the chemical elements found in the return drilling fluid when drilling a geothermal well, for every 10 or 20 meters, and plotting their concentrations relative to the drill depth. The chemical elements which are analyzed are the ores found in the fluids contained in the aquifers. The log is useful for obtaining information as to what type of aquifer the drill bit has penetrated, the relative temperature of the aquifer and the composition of the aquifer water. The log obtained here is for the composition of formation water which flows into the borehole, ie, it is specifically designed for formation waters. Consequently, no information is provided on the drilling mud used while drilling a well and on the chemical interactions between the mud and the formations penetrated by the wellbore.

The article entitled "Determination of free chromate in liquosulfonate dispersants by ion chromatography with atomic absorption spectrometric detection" and published in Analytica Chemica Acta, 160 (1984), pages 263–266, describes a method using ion chromatography for determining free chromate in borehole additives used in drilling muds. This method is however used in a laboratory, not at the well site, for only one species and the drilling mud is not continuously monitored.

On the other hand, a test, called in the industry the methylene blue test, is currently used to measure the cation exchange capacity (CEC) of the mud solids. It is known that smectite clays have a high chemically-active surface area compared with other clays. This is reflected in the amount of positively charged substances which smectites can adsorb. By measuring the amount of charge which a clay/shale adsorbs one can obtain the cation exchange capacity and this may be used as an indication of its water sensitivity in the borehole. Rough field methods for CEC based on the adsorption of dyes, mainly methylene blue, have been used in the industry for many years. The value of such a test is very limited because the method does not allow the exchange cations associated with the exchange sites to be identified and their contribution to the ionic content of the mud system cannot be assessed. The measured CEC of clay minerals determined by the methylene blue test also depends on the nature of the exchange cation.

One object of the invention is to control the drilling of boreholes by determining the ionic compositions of the drilling muds and/or drilled cuttings in order to monitor various chemical processes which occur in the wellbores, eg salt water influxes, changes in the solubility of salts with changes in pH and cation exchange processes involving the cations added to the water-base mud (eg potassium, calcium) to stabilize shale sections.

According to one aspect of the invention, the mud is sampled and its aqueous filtrate is analyzed at the rig site by ion chromatography for determining selected positive and negative ion concentrations. In addition, the pH and the temperature of each sample can be measured. In a preferred embodiment, the anion, monovalent cation and divalent cation contents of the mud sample filtrate are determined by three chromatography units. Preferably the composition of the mud filtrate thus monitored is interpreted to indicate downhole interactions, with the composition of the mud supplied to the hole being adjusted to or towards the optimum as drilling proceeds.

According to another aspect of the invention, changes in lithology or other changes as drilling proceeds are determined by cross-plotting the calcium and magnesium ion concentrations of the samples and/or by cross-plotting the potassium ion concentration or the potassium/sodium ion concentration ratio and the calcium/magnesium ion concentration ratio of the samples. In another aspect of the invention, the drilling mud in use is tested by analyzing at the rig site the mud solids of the periodically sampled mud for sorbed ions and/or for cation exchange capacity. The mud solids are dried, a known weight of the dried solids is washed to remove sorbed ions, and cation(s) and anion(s) in the resulting solution are identified and assayed by ion chromatography.

In a further aspect of the invention, the drilled cuttings in the drilling mud in use are analyzed by separating the cuttings from the mud, drying, extracting ions from a known weight of the separated dried cuttings into solution, and analyzing the resulting solution by ion chromatography for selected positive and negative ions. The cation exchange capacity of the drilled cuttings can then be advantageously determined.

In another further aspect of the invention, the circulating mud is periodically sampled, its aqueous filtrate is analyzed at the rig site for determining selected positive and negative ion concentrations, the ion concentration data are stored and compared with already stored data. These stored data can be the data previously acquired by the analysis of preceding mud filtrate samples or can be reference data characteristic of the required mud formulation.

The following description of the invention is accompanied by drawings in which:

BRIEF DESCRIPTION OF THE DRAWINGS

FIG. 3 is an example of the output of an ion chromatograph;

FIG. 4 shows a sample format of the mud composition log;

FIG. 6 is a sample format of the mud solids log;

FIG. 7 is a sample format of the cuttings log;

Referring to FIG. 1, which shows the mud circulation equipment, the mud 10 is contained in a mud pit 12, called the active tank. A pump 14 draws up the mud from the pit through a pipe 16 and forces the mud through the discharge line 18, the stand pipe 20, the rotary hose 22 and the swivel 24. The mud then flows into the kelly 26 and down the borehole 28 in the drill pipe 30 and the drill collars 32. The mud reaches the bottom of the hole at the drill bit 34 and then flows up to the surface in the annulus 36 and in the mud return line 38. The mud then falls over a vibrating screen-like device 40, called a shale shaker. The role of the shale shaker is to separate from the liquid phase of the mud, the cuttings drilled by the bit 34 and transported up in the annulus by the mud. The separation is made by having the mud passing through a screen which vibrates. The solids, called the cuttings, which are larger than the mesh size of the screen don't pass through the screen and are rejected either in a reserve pit when the drilling rig is on land or in a barge when the drilling operations are conducted offshore. The solid particles contained in the mud which have a size smaller than the mesh size of the screen pass through the screen and therefore remain in the mud. These fine solids (hereinafter referred to as the mud solids or the solids) comprise part of the weighting material added to the mud to reach a certain mud density and also fine solids from the formations traversed by the borehole. After the shale shaker 40, the mud flows into solids control equipment, represented schematically by 42, through the pipe 44. The solids control equipment 42 could include a degasser, a desilter and a desander. Then the mud falls into the pit 10 through the pipe 46. A mud-mixing hopper 48 is generally used to add solid materials like clay and barite to the mud in the active tank.

Figure 1:
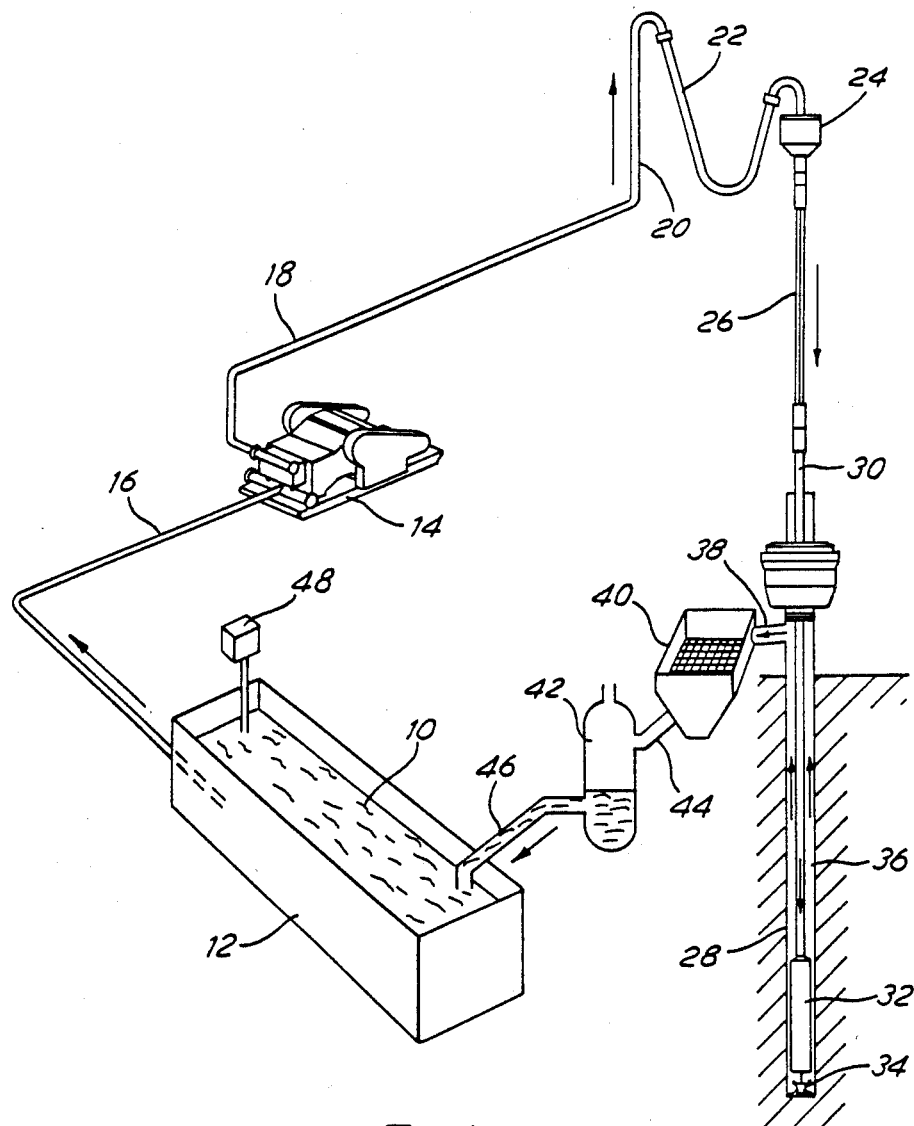
FIG. 1 shows schematically the circulating system of the mud used in the oil rigs.

The following description of the invention refers to experiments which have been made with mud samples taken at known times and every 15 minutes, from both the active tank 12 and from the pipe 44 between the shale shaker 40 and the solids control equipment 42. In addition, samples of cuttings have been obtained directly in the shale shaker 40. Analyses are done on the mud filtrate in order to determine its ionic composition and on the mud solids and the cuttings for which the cation exchange capacity is determined. The analytical technique is preferably an ion chromatograph system, used to determine both the cation and anion contents of the mud and of the cuttings, and the cation content of the mud solids. Usually the ionic content is determined on clean, solid-free solutions, and consequently solid-liquid separation is required for most of the analyses. The principal ions of interest are potassium, sodium, calcium, magnesium, chloride, sulphate and bromide. The ion composition of the mud filtrate is augmented by the hydroxide ion content determinable from rig site measurement of pH on both the mud and the mud filtrate. The interpretation of the measurements made on the mud filtrate is made at the rig site, preferably with the aid of a computer.

A major advantage of the ion chromatography technique is its ability to identify anion species, in contrast to most other techniques (eg atomic absorption spectroscopy, flame emission photometry, inductively coupled plasma [ICP]). Further advantages of an ion chromatography system are its sensitivity (resolution down to about 1 part per billion), precision (better than 0.5% based on peak area) and ability to differentiate ionic species with generally small interference effects. The principles of operation and general use of an ion chromatograph are well known.

Figure 2:
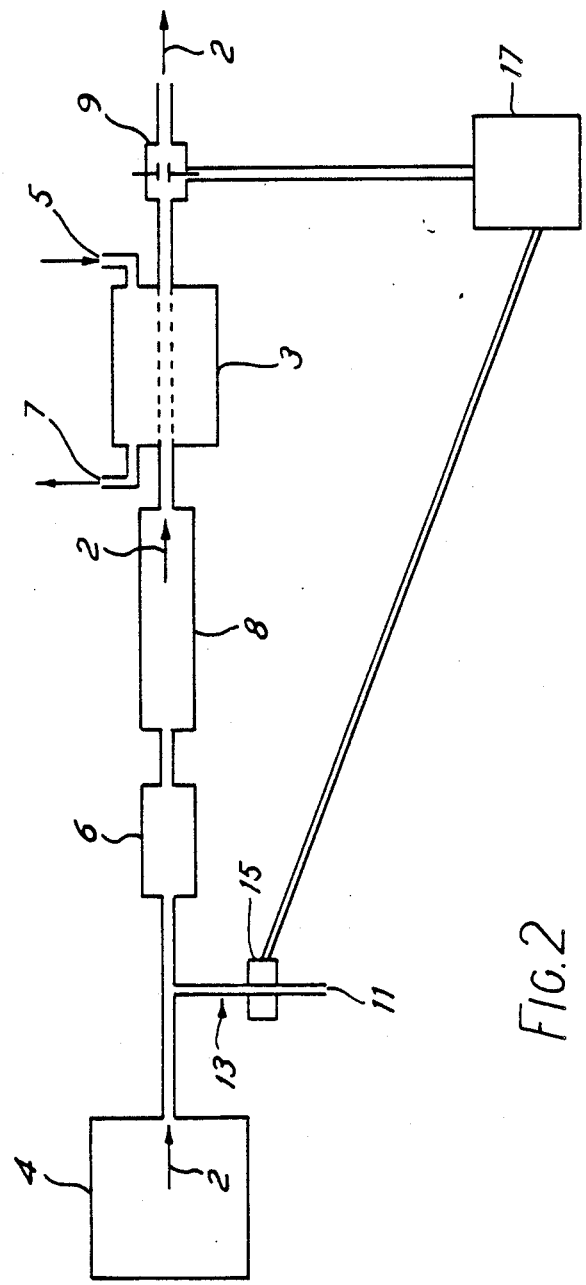
FIG. 2 illustrates the ion chromatography unit.

The rig chromatography system can have preferably three independent units allowing the simultaneous determination of anions, and monovalent and divalent cations. Each unit may have a chromatography pump, an injection system with a fixed volume injection loop, an ion exchange column, a suppressor fibre or membrane, and an electrical conductivity detection system. FIG. 2 shows schematically such a unit in which there is eluent flow 2 from a high pressure liquid chromatography pump 4 through a guard column 6, ion exchange column 8, suppressor membrane unit 3 having regenerator inlet 5 and outlet 7, and finally conductivity detector 9. The suppressor is used to reduce the electrical conductivity of the eluent employed to separate the ionic species in the chromatography columns and therefore to increase the resolution of the measurements. On FIG. 2, a "chemical" suppressor is shown schematically, but an "electronic" suppressor can be used as well. The injection system includes an injection port 11, fixed volume injection loop 13 and injection timer 15, and connected between the detector 9 and timer 15 is an output system 17 which reports conductivity as a function of time. The electrolyte solution to be analyzed, which has been separated from its associated solid phase, is injected into the three chromatography units simultaneously either manually or using an autosampler with a triple connector. The output from the three separate detector systems can be logged by computer. The particular ion species are identified by their characteristic retention times in the ion exchange columns, while their concentrations are determined by the integrated areas under the peaks. A computer can give a direct reading in concentration units if it is programmed with calibration data consisting of peak area as a function of concentration. For optimal performance, the standards are matched to the approximate compositions of the samples to be analyzed. FIG. 3 shows a typical example of the output of an ion chromatography system (note that the scaling of the peak heights of the three ion types has been adjusted for the convenience of the display) used according to the invention. FIGS. 3(a), 3(b) and 3(c) are examples of plots obtained for divalent cation, monovalent cation and anion analysis, respectively.

In the present invention, a mud filtrate ion may be a "principal" ion and of interest for one or more of a number of reasons. For example it may have a concentration in the filtrate of at least 100 ppm. It may have a significant effect on mud properties at any concentration, which is frequently the case when it is a deliberate special additive to the mud; it might be one giving rise to potential environmental problems if discharged even at low concentrations—eg well below 100 ppm. All mud filtrate ions of interest could be assessed by ion chromatography but are not necessarily. Thus hydrogen and hydroxyl ion concentrations can be provided by pH measurement, and carbonate and hydrogen carbonate (bicarbonate) ion concentrations can be deduced from the measured concentrations of other ions. Of the principal mud filtrate ions present which are suitable for ion chromatography, not all need be measured, though at least one cation concentration and at least one anion concentration are measured in this way. Typical principal mud filtrate ions for assay by ion chromatography are sodium, potassium, calcium, magnesium, chloride and sulphate.

At the locations where the samples are taken, the pH and temperature of the mud are measured and logged by a combined probe inserted into the mud stream. Each mud sample is transferred to a centrifuge where the solid and liquid components are separated at a fixed rotation speed and for a fixed period of time. The mud filtrate is injected into the three ion chromatography units simultaneously to determine its anion, monovalent cation and divalent cation contents. In general the mud filtrate must be diluted by a factor of about 100 to ensure that the analyte concentration is in the optimum range of the ion chomatography system. The pH of the mud filtrate (undiluted) is determined at ambient temperature and corrected to the value at the temperature recorded at its sample point.

A correction is required to convert the measured composition of the filtrate to a total ionic composition of the mud which expresses the ionic composition per unit volume of mud $$C_i^m = v_a C_i^f \tag{1}$$

where $C_i^m$ is the concentration (moles m$^{-3}$) of the ionic species in the mud, $C_i^f$ its concentration in the filtrate as determined by the ion chromatography system, and $v_a$ the volume fraction of aqueous phase in the mud. The volume fraction $v_a$ is defined by $$v_a = \frac{V_a}{V_m} \tag{2}$$

where $V_a$ is the volume of aqueous phase in a total volume of mud $V_m$. In the absence of dilation effects on mixing the mud solids (volume $V_s$) with the aqueous phase $$V_m = V_a + V_s \tag{3}$$

giving the volume fraction vs of solids in the mud $$v_s = 1 - v_a \tag{4}$$

A simple rig site method of determining $v_a$ consists of a combination of a measurement of the mud density and the weight fraction $w_a$ of the aqueous phase in the mud which is defined by $$w_a = \frac{M_a}{M_m} = \frac{M_w + M_e}{M_m} \tag{5}$$

where $M_a$ is the mass of the aqueous phase (composed of mass $M_w$ of water and $M_e$ of dissolved salts) in mass $M_m$ of mud. Thus, $$w_a = \frac{V_a d_a}{V_m d_m} = v_a (d_a/d_m) \tag{6}$$

where $d_a$ and $d_m$ are the density of the aqueous phase and mud, respectively. A quantity $w_a'$ is defined by $$w_a' = \frac{M_w}{M_m'} \tag{7}$$

such that $$w_a = w_a' + (M_e/M_n) \tag{8}$$

$$w_a = w_a' \left[ 1 + \frac{\Sigma_i C_i^f M_i^m}{d_w} \right] \tag{9}$$

where $M_i^m$ is the molar mass of ion i (kg per mole) and $d_w$ is the density of water (kg m$^{-3}$). The quantity $w_a'$ can be measured accurately and quickly using a small infrared drying balance to dry the mud sample to constant weight at a fixed temperature. The required weight fraction $w_a$ can therefore be calculated from equation (9). The mud density $d_m$ can be determined from a conventional densitometer (or an oilfield mud balance) while $d_a$ can be accurately calculated from the known ionic composition of the mud filtrate.

Figure 4:
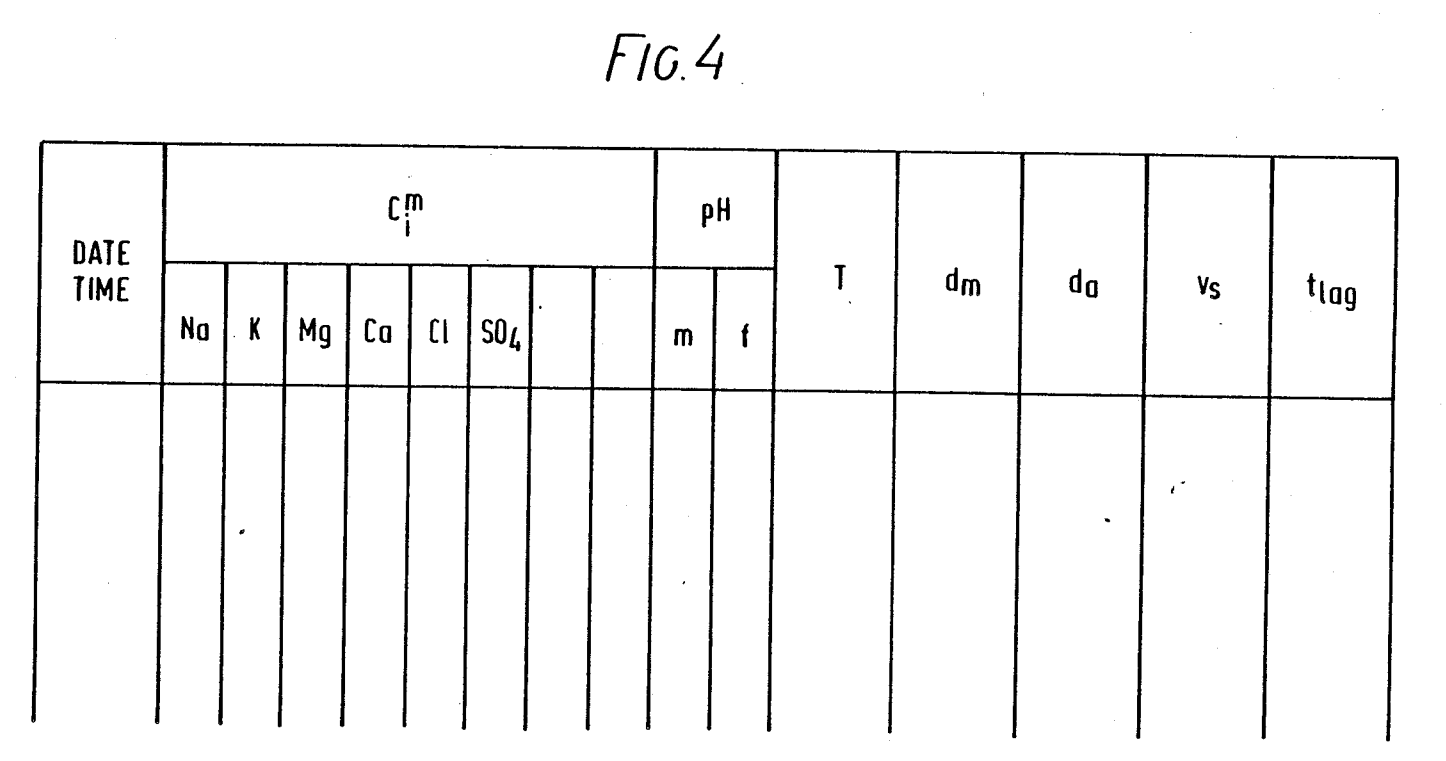

The corrected output from the filtrate analysis using the ion chromatography system is the set of $C_i^m$ for the major anions and cations (typically sodium, potassium, calcium, magnesium, chloride and sulphate) in the mud system. The set $C_i^m$, together with the measurement of pH and temperature of the mud stream at the sample point, pH of the mud filtrate at the mud stream temperature, mud density $d_m$, and the volume fraction $v_s$ of solids in the mud are reported together with the sample time and the mud lag time. The format of the data is a multi-track log, the mud composition log, showing the value of each individual measurement as a function of time. FIG. 4 shows a sample format of the mud composition log. The values of $C_i^f$ are available to enable filtrate composition to accompany the API recommended filtration test (API RP 13B, 1980). The lag time $t_L$ is defined later on by equation (28).

It is possible to optimize the flow rate and concentration of the eluent in the ion chromatography system to obtain good quality chromatograms over a short time period. For the chromatography system described, it is possible to measure the set of $C_i^f$ approximately every 15 minutes, giving about four mud analyses each hour.

Mud solids may be analyzed instead of or in addition to the mud filtrate. As already indicated, the current practice in the oilfield on the analysis of the solid component of the mud is the determination of its cation exchange capacity (CEC) using the methylene blue test. The main object of the test is to determine the buildup of dispersed clay minerals from drilled shale whose particle size is too small for removal by the drilling rig's solids control equipment. In accordance with the invention, an ion chromatography system is used to provide an accurate measure of the CEC of the mud solids and to identify the exchange cations of the clay minerals during the drilling process.

For example, a known weight of the centrifuge sediment is dried at a fixed temperature to constant weight. The dry sediment is homogenised and then washed with a known volume of aqueous methanol or water to remove the sorbed salt without hydrolysis of the exchange cations on the clay surface. The methanol-water-salt solution or water-salt solution is diluted by a factor of about 100 and analyzed for anions and cations using the ion chromatography system. The concentration of sorbed ions in the sediment, expressed as moles of ion per kilogram of dry mud solid, is noted. The sorbed ion content is generally found to be negligible in comparison with the concentration of the ion in the filtrate, particularly at high centrifuge speeds. However this assumption is continually checked, and when high sorbed ion contents are encountered a correction can be made.

Having determined the sorbed ion content, the cation exchange capacity of the mud solids may be determined and the exchange cations identified.

For example, a known weight of the dry, washed mud solid sediment (homogenised) is mixed with a known volume of 0.5 molar tetramethylammonium bromide solution. The large excess of tetramethylammonium ions will replace the naturally-occurring exchange cations on the mud solids and release them into the exchange solution. A neutral to high pH is required to ensure that the release of calcium ions into solution by the dissolution of calcium carbonate is minimized. After a fixed time, the ion exchange suspension is centrifuged at a fixed speed for a fixed time and the supernatant extracted. The separated solid is then reacted with a second known volume of the tetramethylammonium solution to ensure complete exchange. The two supernatants are combined, diluted by a factor of about 100 and analyzed for monovalent and divalent cations by the ion chromatography system. The sum of all the cations released, normalized to dry solid weight, is therefore the cation exchange capacity of the mud solids, expressed in moles of monovalent exchange sites per kilogram of dry solid. The exchange cations associated with the mud solids may be considered to be an integral part of the cations in the mud system. The contribution $C_i^{ms}$ of exchange cation i in the mud solids to the total content of i in the mud is given by $$C_i^{ms} = \overline{x}_i CEC(1-w_a)d_m, \quad (10)$$

where $x_i$, is the fraction of the cation exchange capacity (CEC) of the mud solids occupied by cation i.

The density $d_s$ of the dry solid component of the mud can be calculated from $$d_m = v_a d_a + v_s d_s \quad (11)$$

since the quantities $d_m$, $d_a$, $v_a$ and $v_s$ are all known.

Figure 5:
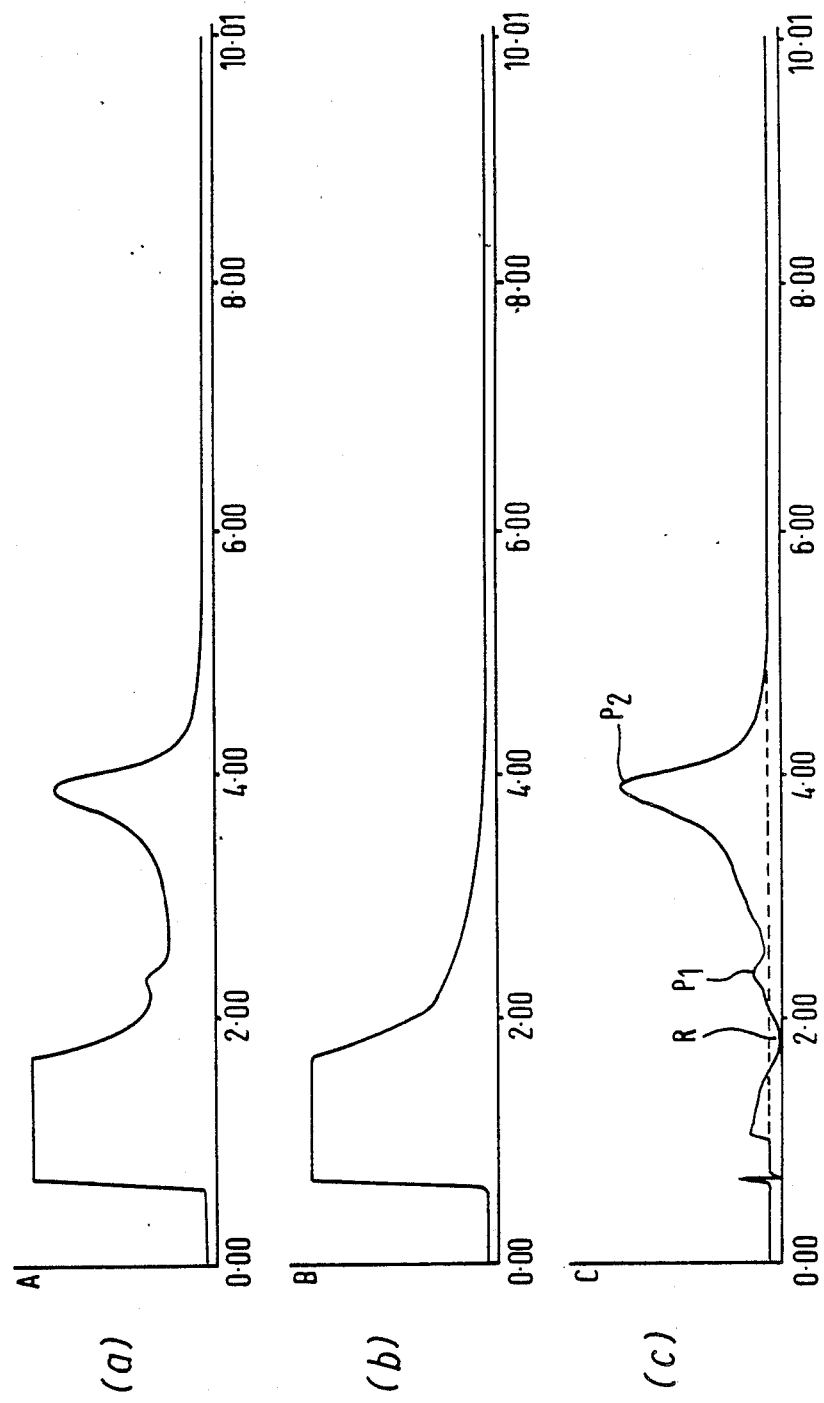
FIG. 5 illustrates briefly the procedure used to check on the cation exchange capacity of the mud solids.

A check on the cation exchange capacity of the mud solids can be made by measuring the difference in the tetramethylammonium ion concentration before and after the ion exchange reaction with the solids. FIG. 5 shows a summary of the procedure. FIG. 5(a) shows the raw chromatograph for the release of divalent cations from the ion exchange reaction together with the large excess of tetramethylammonium ions which have not been exchanged. The chromatograph of the original 0.5 molar tetramethylammonium solution is shown in FIG. 5(b). The subtraction of FIG. 5(b) from FIG. 5(a) gives FIG. 5(c) which shows not only the positive peaks $P_1$ and $P_2$ of the released magnesium and calcium cations respectively, but also the removal R of tetramethylammonium ions from the reaction solution. The charge of the released cations is directly compared with the charge of the tetramethylammonium removal.

The output of the measurements on the mud solids is a multi-track log termed the mud solids log, and shows the CEC, the volume fraction $v_s$ of solids in the mud, the density $d_s$ of the dry solid component, the fraction $x_i$ of cation i saturating the exchange sites, its effective concentration $C_i^{ms}$ in the mud system and the change $\Delta C_{ms}$ in the exchange capacity of the mud solids for each sample time. FIG. 6 shows a sample format of the mud solids log. Drilled shale cuttings may usefully be analyzed, independently or in addition to the mud filtrate and/or solids analysis.

A problem which is faced in the design and use of an inhibitive mud system is that the nature of the shales which are to be controlled is often unknown. Since different shale types generally require different inhibitive mud compositions, the effectiveness of the mud in the shale formations is unknown. One solution to the analysis and characterization of shales is the use of wireline log data in offset wells or real-time MWD (measurement while drilling) measurements, although the current interpretation of these measurements in shale sections is generally poor.

The alternative solution is the analysis of the shale cuttings at the surface on samples where little degradation (eg, swelling) has occurred during transport in the annulus. Current techniques of cuttings analysis are restricted to geological description (eg conventional mud log), density measurement and the determination of CEC using the methylene blue (or related stain) test. The methylene blue test for measuring the CEC of clay minerals, together with its limitations, has been discussed. Currently no use is made of these measurements for interpretation or prediction of wellbore stability.

An ion chromatography system can be used according to the present invention to provide a rig site measurement of the ionic composition of drilled cuttings, more especially (but not exclusively) shale cuttings, which results in a reliable measurement of CEC and the identification and quantification of the cations available for ion exchange with the mud system.

For example, a sample of drilled shale cutting is taken from the shaker screen and broken up to reveal a portion of the cutting where it appears that no alteration in water content or ion composition has taken place. The shale cutting is dried to constant weight at a fixed temperature using the small infrared drying balance to give the uncorrected fractional weight content $\overline{w}_a^*$ of water in the cutting $$w_a^* = \frac{\overline{M}_w}{\overline{M}_{sh} + \overline{M}_{sa}} \quad (12)$$

where $\overline{M}_w$ is the weight of water lost on drying, $\overline{M}_{sh}$ is the dry weight of the salt-free shale and $\overline{M}_{sa}$ is the weight of sorbed salt ("pore water" salt) within the shale. Measurement of $\overline{w}_a^*$ will be the first (and probably the best) indication that the cutting sample being examined has undergone no change in composition in the annulus.

The dried shale sample is then crushed to produce a powder of a fixed average particle size. The ground shale is washed with a fixed volume of the methanol-water solution or water to remove the sorbed salt without hydrolyzing the shale's exchange cations. The methanol-water-salt solution or water-salt solution is diluted by a factor of about 100 and analyzed for anions and monovalent and divalent cations using the ion chromatography system. The weight $\overline{M}_i$ of each ion per unit weight of dry shale matrix can therefore be determined; the sum of the $\overline{M}_i$ gives the weight of sorbed salt $\overline{M}_{sa}$ from which $M_{sh}$ can be calculated. The corrected weight fraction $\bar{w}_a$ of water in the shale can be obtained from eqn (13)

$$\frac{1}{\bar{w}_a} = \frac{1}{w_a^*} - \frac{M_{sa}}{M_a} \quad (13)$$

noting that $$\bar{M}_{s}a = \Sigma_i M_i \quad (14)$$

The molal concentration (moles of ion per kilogram of water) $\bar{m}_i$ of the sorbed ions i in the shale is obtained by normalizing the $\bar{M}_i$ to the fractional weight of water $\bar{w}_a$ in the shale $$m_i = \frac{M_i}{M_i^m \bar{w}_a}, \quad (15)$$

where $M_i$m is the molar mass of ion i.

The second stage of the analysis of the shale cutting is to determine the cation exchange capacity of the shale and to identify the exchange cations. A known weight of the dry, salt-free ground shale cutting is placed in a known volume of 0.5 molar tetramethylammonium bromide solution and mixed for a fixed time. After the fixed time, the ion exchange reaction is terminated by centrifuging the dispersion at a fixed speed for a fixed time. The supernatant is removed from the centrifuge, and the sedimented solid is dispersed into a second known volume of the ion exchange reaction mixture to ensure complete exchange. The combined reaction solution is diluted by a factor of about 100 and analyzed for monovalent and divalent cations using the ion chromatography system. The identification and quantification of the cations in the ion exchange liquor is obtained; the summation of all the released cations is the cation exchange capacity CEC. The method of chromatograph subtraction to establish charge balance in the ion exchange process, shown in FIG. 5, is also applicable to the measurement of the CEC of shale samples.

The cuttings analysis can be presented in the following format. The total cation content of the cuttings (obtained as exchange or sorbed cations) is expressed as the molal concentration $\bar{m}_c$, while the sorbed anion content $\bar{m}_a$ is simply obtained from the initial washing procedure. In both cases, the molal concentrations are with respect to the water content in the cuttings. The difference between the anion and cation content of the cuttings is due to the cation exchange capacity CEC, $$\Sigma m c_c Z_c - m_a Z_a = A = \frac{CEC}{w_a} \quad (16)$$

where $Z_c$ is the charge on a cation, $Z_a$ is the charge on an anion, and A is the effective concentration of univalent ion exchange sites in the cuttings normalized to the water content. The output of the measurements is the cuttings analysis log which gives the cuttings water content $\bar{w}_a$, anion and cation molal concentration $\bar{m}_i$, the CEC, and the value of A for each cuttings sample. The time at which the sample was taken from the shaker screen is converted to formation depth using an annulus lag time. The lag time used to relate sample time to formation depth is shown on the cuttings analysis log. An example of the format of the cuttings log is shown in FIG. 7.

The measurement of the ionic composition of one or more of the mud filtrate, mud solids and drilled cuttings is accompanied by a rig site (eg computer-based) interpretation giving continuous information on the chemical composition of the mud and the extent of mud-formation interactions. Various interpretation schemes are discussed separately below.

(1) Mud Filtrate Composition

Figure 8:
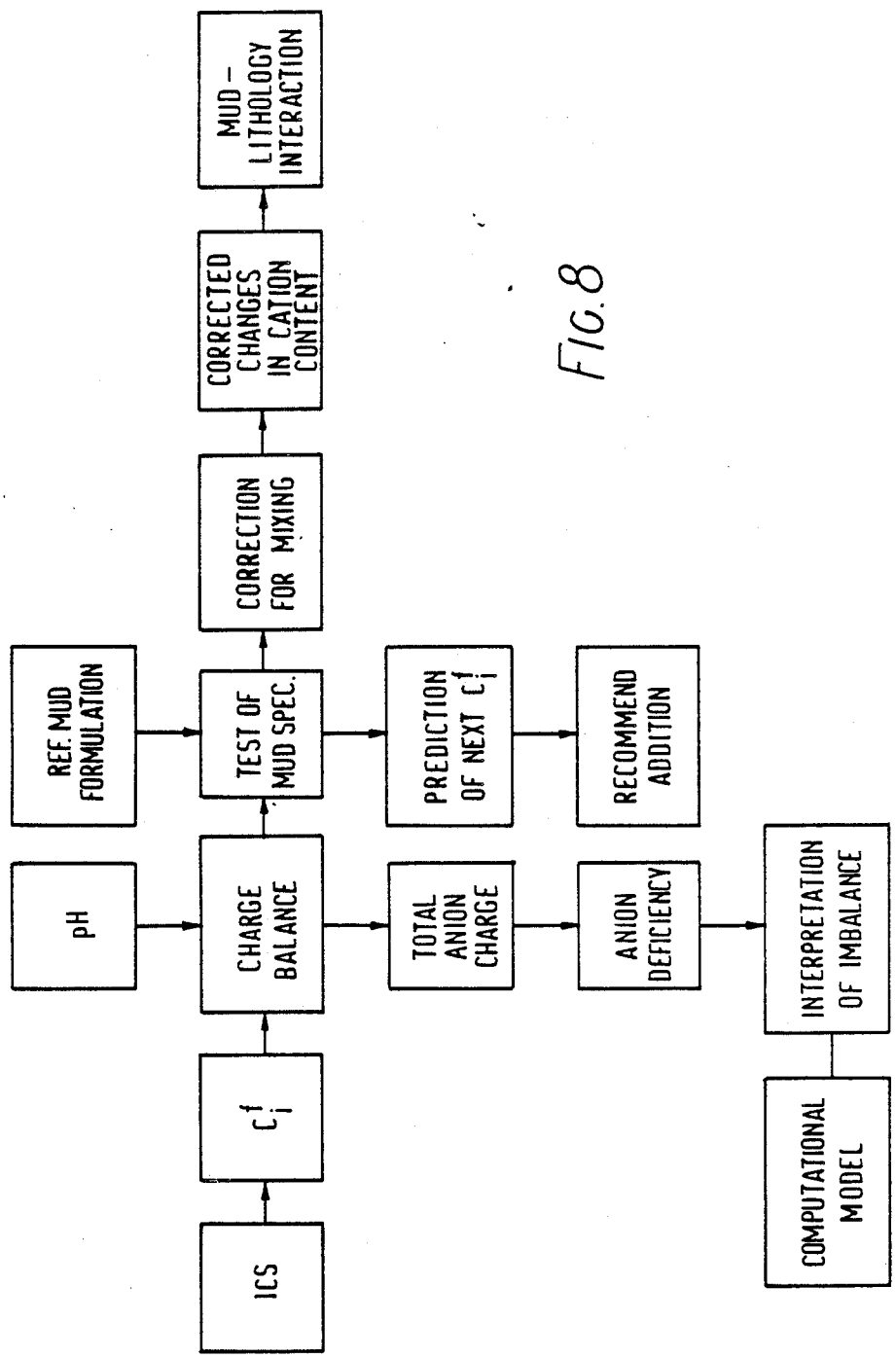
FIG. 8 illustrates an algorithm for an interpretation scheme for the mud filtrate analysis.

FIG. 8 shows an algorithm for an interpretation scheme, hereinafter called the "mud advisor system", for the mud filtrate analysis based on the rig site measurements of $C_f$ and filtrate pH. After each mud analysis (ie at intervals of approximately 15-20 minutes) the main outputs of the data interpretation system are:

(a) recommendations to adjust salt content and pH of mud to maintain the specification;
(b) trend analysis on changes in filtrate composition to indicate mud-lithology interactions.

After each analysis, the mud filtrate composition $C_f$, mud and filtrate pH, mud density and volume fraction of solids in the mud are compared with the equivalent values for the mud which has been specified (reference mud). The mud formulation has been analyzed at some specified temperature to determine $C_f$, pH (mud and filtrate), $d_m$ and $v_s$ which will act as reference values; the filtrate from the reference mud formulation is run regularly to check the calibration of the ion chromatography system. Each analysis therefore yields the difference between the mud sample and the reference. If the formulation of the mud specification is accompanied by bounds within which the composition and properties are acceptable, then the analysis of the mud will determine when the mud is out of specification.

The "mud advisor system" requires additional data to enable changes in mud filtrate composition and mud properties to be converted into recommendations in changes to the mud system, and to diagnose downhole and formation-mud interactions. The required data are:
mud flow rate
open hole volume
total hole volume
total ionic compositions of all additions to mud (solids and
liquids)
drilled lithology
the drilling rate of penetration (ROP).

Over some specified time period where n analyses of mud filtrate have been performed ($\sim$n/4 hours), trends in the change of ionic composition (including pH) are constructed.

An average rate of change of species $C_f$ is calculated for the n data points. If the trends are well identified, then the "mud advisor" can predict the results of the next analysis, ie the set of $C_f$. The (n+1) (ie, next) analysis can be checked with the mud advisor's prediction for each measurement. A quantity $\Delta i^{n+1}$ can be defined which measures the deviation, within bounds set by the quality of the trend identified from the previous n points, from the mud advisor's prediction. The trend and its quality are compared with the ROP, mud flow rate and the drilled lithology over the same time period to establish if there is any recognizable cause for the trend and the reasons for the calculated deviation $\Delta i^{n+1}$. The "advisor" can display the mud composition log showing the n points for the operator to visually examine the trend.

Assuming that the mud is within the desired specification for the n analyses, then the "mud advisor" system can predict the time $t_s$ when the mud will move out of specification for a particular ion species. Clearly some ionic species have a greater weighting than others, and the weighting expresses the role of the species in the performance of the mud. For example, it may only be necessary to maintain the concentration of potassium, magnesium, sodium and calcium ions together with the pH; the variation of the bromide content within reasonable bounds may therefore be of little interest. The "advisor" uses the trend in the $C_f$ to calculate the necessary batch addition of salt to the mud to prevent violation of the mud specification or to correct the composition if the specification is already violated. If the concentration change indicated by the "advisor" is dC, then the required amount of salt to return the mud to specification is $V_T \cdot dC$, where $V_T$ is the total volume of the active mud system. The volume $V_T$ is known, which together with the mud flow rate $v_m$, enables the round trip time $t_R(=V_T/v_m)$ of the mud to be calculated and hence the time required for the addition to be registered on the mud composition log. To maintain the specification of the mud, based on the advisor's predictions, it is required that $t_s$ is larger than $t_R$.

The general problem which is faced in attempting to interpret changes in $C_f$ is to be able to distinguish between hydrodynamic dispersion (including dilution from significant additions of fluid to the mud) and reaction (adsorption, precipitation, etc) in the wellbore. Since one of the main objectives of the "mud advisor" system is to indicate mud-formation interactions, it is necessary to discriminate between hydrodynamic dispersion and borehole reaction. The problem of hydrodynamic dispersion may be addressed by using a tracer chemical in the wellbore which is detectable by the ion chromatography system but more or less inert with regard to borehole reactions such as adsorption or precipitation. An example of such a chemical is lithium bromide, the lithium and bromide ions being readily detected by the ion chromatography system and not subject to solubility changes as the pH of the mud varies. The lithium ion is of sufficiently low ion exchange selectivity to minimize interaction with the formation or cuttings.

The use of a specific tracer to determine the dispersion characteristics of the wellbore involves the measurement of its concentration $C_f$ in the filtrate as a function of time. It is required that the input concentration characteristics of the tracer are known such that the wellbore transfer function can be determined. For example, a known amount of the tracer is uniformly injected into the mud flow system for a fixed time, which for a given mud flow rate enables the concentration step of the tracer to be calculated. The measurements of the concentration $C_f$ of the tracer in the return mud flow will enable the dispersion characteristics of the wellbore to be determined. The input concentration for the addition of each active mud chemical to the mud flow system must be similarly measured, and the "mud advisor" can be used to control the input from a knowledge of $V_T$, $d_C$ and $t_R$.

The use of an inert tracer ion to monitor the dispersion factor in mud circulation is the subject of our co-pending UK patent application No 8,705,503 filed on 9 March 1987 and entitled "Monitoring Drilling Mud Circulation".

The second major task which the rig site "mud advisor system" performs is an attempt to explain the changes in the ionic composition of the mud in order to identify the various downhole processes.

The first step is to identify the purely dispersive contribution to the change in $C_f$ from simultaneous measurement in $C_f$. It should be emphasized that the variation of $C_f$ with time does not generally constitute the normal type of dispersion curve (obtained, for example, from a carbide lag test), since the measurement of $C_f$ by the ion chromatography system is not continuous. However the filtrate is sampled at the same time as the tracer so that a direct comparison between the transport of inert and active species can be made. The measurement of $C_f$ by the ion chromatography system could be used to calibrate continuous but less direct measurements of concentration in order to obtain the dispersion characteristics of the well. An example is the use of lithium and bromide ion selective electrodes which can be combined with the pH measurement system.

An alternative approach is to use the "mud advisor system" to calculate the amount of species i to add continuously (ie not batch addition) to the mud stream such that the $C_f$ remain constant, or at least within the bounds set by the mud specification. This addition is obtained from knowing $V_T$, dC and $t_R$ at each analysis. The addition of species i to maintain the specification of the mud system is therefore a direct measure of its uptake resulting from interactions in the wellbore.

The second step is the quantification of the apparent charge deficit to indicate the importance of anions such as carbonate and bicarbonate which are not routinely detected by the ion chromatography system described above. Charge balance in the measured mud filtrate composition requires that $$\Sigma_i C_f Z_i = 0 \tag{17}$$

where $Z_i$ is the charge of ion i. The ion chromatography system as described does not detect hydroxide ($OH^-$), carbonate ($CO_3^{2-}$) and bicarbonate ($HCO_3^-$) anions. Since these anions are present in the mud system, the analysis will appear to show an anion deficiency. The measurement of pH will allow $OH^-$ to be determined since $$\log_{10}[OH^-] = pH - 14 \tag{18}$$

With muds which are sea water based, the charge balance equation (eqn (17)) will involve the ions sodium, potassium, calcium, magnesium, chloride, sulphate, bromide and hydroxide (ie, pH). The anion deficit $A_d$ is determined from $$A_d = \Sigma_c C_f Z_i + \Sigma_a C_f Z_i' \tag{19}$$

where the subscripts c and a indicate summation over the cation and anion species, respectively, as identified and measured by the ion chromatography system and pH measurement. If the anion deficit $A_d$ is above a certain value, and this value is chosen such as to account for the gross precision of the anion analyses and typical concentration of the less important anions (eg, fluoride, sulphide) and cations (eg, strontium), then it is reported as significant by the "mud advisor" and displayed after each analysis.

The interpretation of the levels of carbonate and bicarbonate anions and the magnesium and calcium cations in the mud filtrate requires an understanding of a number of complex chemical reactions which are dependent on the pH of the mud system. The solubility of calcium ions, for example, is determined by two major equilibria, namely, the precipitation of solid calcium hydroxide (lime, $Ca(OH)_2$) and solid calcium carbonate ($CaCO_3$). The pH dependence of the calcium ion concentration as given by the reaction $$Ca(OH)_2 = Ca^{2+} + 2OH^-, \quad (20)$$

or $$Ca(OH)_2 + 2H_+ = Ca^{2+} + 2H_2O, \quad (21)$$

is determined, at 25°, by $$\log_{10}[Ca^{2+}] = 22.8 - 2pH \quad (22)$$

When the pH of the mud increases, the maximum permissible calcium ion concentration in the mud filtrate decreases. In most typical muds where the pH is about 10 or less, the equilibrium calcium concentration can be very large so that lime precipitation is not a problem. The precipitation of magnesium hydroxide is governed by (at 25° C.)

$$\log_{10}[Mg^{2+}] = 16.84 - 2pH, \quad (23)$$

so that, for a given pH, the maximum concentration of magnesium is considerably below that of calcium.

The presence of soluble carbonate and bicarbonate anions in the mud system gives rise to a rather more complex interpretation problem. The carbonate level in the mud can be changed by a number of processes, including the uptake of carbon dioxide from either the air (agitation in the solids control equipment and active tank) or wellbore influxes (in the form of gas or solution), carbonate (limestone and dolomite) dissolution and mud additives containing carbonate. In general, the mud system must be regarded as an open system with regard to carbon dioxide.

Within the "mud advisor system" can be a computational model which contains a number of equilibrium chemical reactions of the type shown in eqn (21). This model, which contains a database of equilibrium constants for all of the reactions which are considered relevant to the mud system, can be similar to the models which are well known in interpreting the chemical composition of natural waters, such as the model used in the commercial computer programme known under the name WATEQF. At each analysis, the model is called upon to attempt to explain the trends in the $C_f$, pH and anion deficiency $A_d$. For example, the model and database can be used to calculate the carbonate and bicarbonate concentrations in the mud filtrate assuming that the mud system is in equilibrium with the carbon dioxide in the air and using the measured values of pH, [Ca2+] and [Mg2+]. The calculated carbonate and bicarbonate concentrations can be compared with the measured anion deficiency Ad. Similarly the model can calculate the carbonate and bicarbonate concentrations in the mud based on the measured values of divalent cations and the pH assuming that the mud system is closed and that there is no external source of carbon dioxide. Comparison of these two sets of calculations with the carbonate level as measured by the anion deficiency indicates to what extent the attribution of the anion deficiency to carbonate and bicarbonate ions is valid. The thermodynamic calculations performed within the model include the determination of the partial molar volume of the $C_f$ which enables the density $d_a$ of the filtrate to be calculated (see eqn (6)). The thermodynamic calculations can also yield the activity $a_w$ of the water in the filtrate, an important quantity used in matching mud systems to shale types.

A cross-plot of magnesium against calcium ion concentrations can give a useful guide to the drilled lithology, yielding distinct lines corresponding to different formations. A cross-plot of potassium concentration or potassium/sodium concentration ratio against calcium/magnesium concentration ratio can also distinguish between different drilled formations, and can indicate seawater influx—especially when the potassium content of the supply mud is different from that of seawater.

The anion composition of the mud, as measured by the ion chromatography system described (ie, excluding hydroxide, carbonate and bicarbonate ions), might be expected to remain largely constant since most changes occur in the cation composition. With a sea water based mud, the principal anions (chloride, bromide, sulphate) might not be expected to vary in composition during the drilling process other than by the addition of salts such as potassium chloride. The measured anion content will therefore indicate gross salt changes within the mud system, including any impurities in the mud additives, eg, sodium chloride in carboxy-methyl cellulose (CMC). Ionic impurities in specific batches of mud chemical can be determined at the rig site using the ion chromatography system. After each analysis the total measured anion charge $A_c^m$ is calculated from $$A_c^m = \Sigma_a C_f / Z_i, \quad (24)$$

and displayed by the "advisor". Changes in $A_c^m$ will indicate salt additions (or removals or dilutions by fluid with a different salt content). A particular use of the measured anion charge is to indicate that salt water has entered the wellbore, eg, from a brine kick. Since the salinity of most permeable formations encountered in oilfield drilling is significantly higher than sea water, the measured anion charge will directly show the influx. If the dispersion characteristics of the wellbore are known, then an estimate of the influx concentration can be made.

The changes in the cation composition, when the measured anion composition, pH, anion deficiency and dispersion characteristics have been taken into account, are due to mud-formation interaction, which is principally cation exchange. Any exchange in the corrected cation levels must be charge balanced such that any removal of potassium ions, for example, must be balanced by an equivalent increase in the concentration of another cation such as calcium. These corrected changes will be a direct measurement of the efficiency of an inhibitive water base mud which is used to drill a shale section. The "mud advisor" system displays the corrected cation concentration change after each analysis.

The output from the cuttings analysis log (FIG. 7) can be processed and interpreted to yield valuable information on the type of shale being drilled (eg, swelling, fracturing), its state of compaction and the cations which can be released into the mud system when cation exchange occurs. The output from the shale analysis log can be processed and displayed by the "mud advisor" system.

The first information which the cuttings analysis log presents, when the drilled formation is a shale, is an indication of shale mineralogy from the measurement of the CEC of the cuttings. In general low values of CEC correspond to the hard, illitic/kaolinitic shale types which can give rise to wellbore stability problems by hydration induced fracture. The higher values of CEC correspond to increasingly softer shales which are characterized by a high montmorillonite content and a tendency to give rise to wellbore stability problems arising from swelling and dispersion. The shales with high values of CEC ("gumbo" shales) which undergo dispersion in the wellbore give rise to solids control problems and a rise in the volume fraction of solids in the mud system ($v_s$ in eqn (4)). The CEC of the shale therefore broadly correlates with the value of $v_s$.

Figure 9:
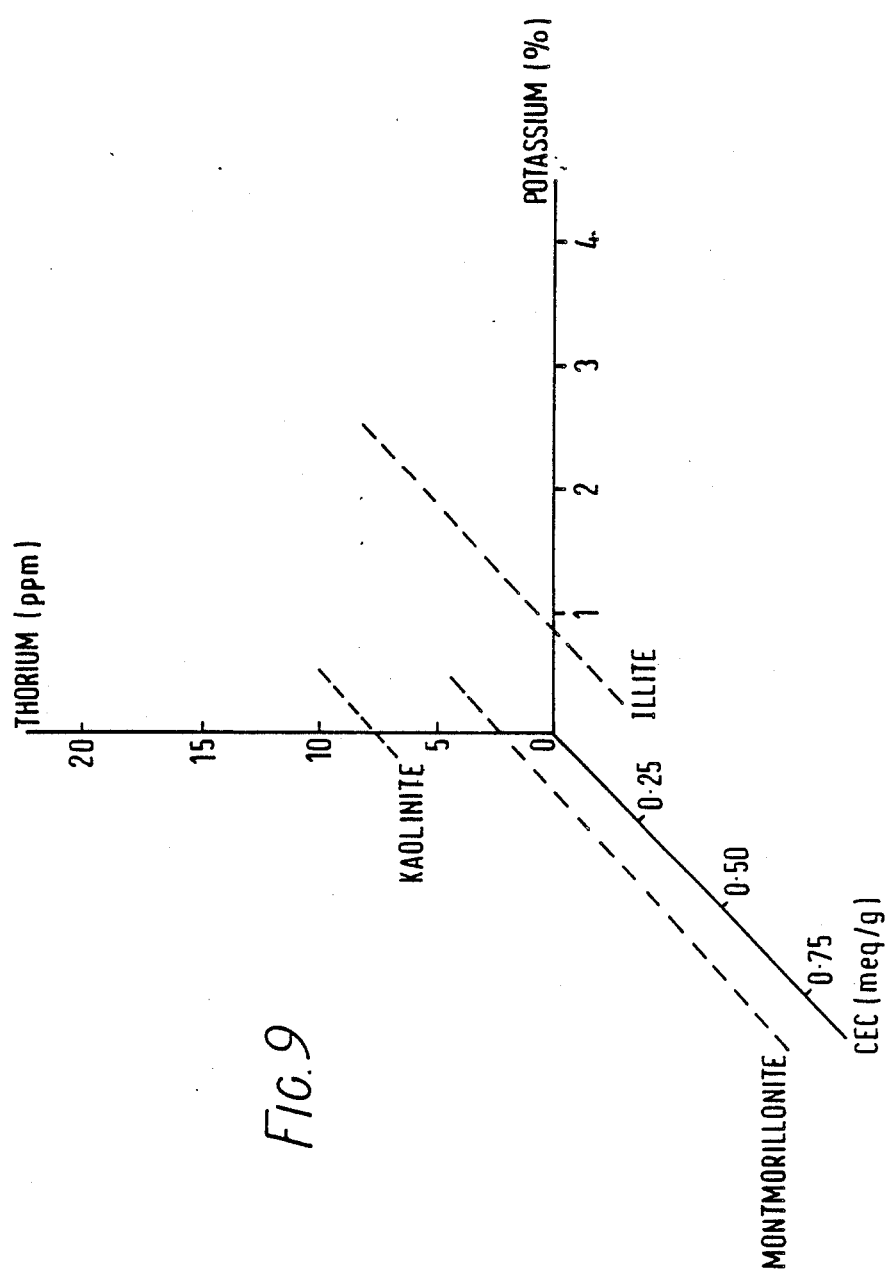
FIG. 9 is a plot where the potassium and thorium concentration axes are supplemented by the measured cation exchange-capacity.

A more detailed mineralogy of shales can be obtained by a combination of the rig site CEC measurement with the mineralogy obtained from the well known potassium/thorium content plot, the comparison being determined by the natural gamma-ray spectrum of the shales. The natural gamma-ray spectrum of the shales is obtained from an MWD spectrometer. The combined plot is shown in FIG. 9 where the potassium and thorium concentration axes (in weight % and ppm, respectively) are supplemented by the measured CEC. A particular advantage of the addition of CEC to the potassium/thorium cross-plot is the identification of shales which contain predominantly kaolinite or montmorillonite, and which are often not well resolved on the potassium/thorium cross-plot. As shown in FIG. 9, montmorillonite shales are characterized by larger values of CEC, compared with kaolinite shales. The combination of the composition from the MWD natural gamma-ray spectrometer and the rig site CEC measurement means that shale mineralogy can be established within a typical lag time from being drilled.

During the burial and compaction of a shale formation, both water and sorbed salts (anions and associated cations) are expelled from the shale into adjacent permeable formations. The water content $\bar{w}_a$ (eqn 13) and sorbed salt content of the shale are expected to decrease with increasing compaction (depth). If the shale cuttings can be considered to have been in at least local equilibrium with the shale formation prior to drilling, then the shale can be treated as a compacting Donnan membrane. From simple Donnan membrane theory, the sorbed salt content is determined by the salt concentration in the adjacent permeable formation and the effective concentration $A$ ($=CEC/\bar{w}_a$) of cation exchange sites.

A major output from the shale analysis log is the variation of water content $\bar{w}_a$ with the vertical depth Z. Within a given shale formation, the compaction trend can be established from direct measurements of water content rather than from values inferred from wireline or MWD log data. If the compaction of the shale has always been accompanied by drainage, then at a given depth Z the water content $\bar{w}_a$ depends only on the mineralogy of the shale and its ionic composition. The mineralogy of the shale section (and any variations within it) is determined from the CEC of the cuttings as displayed on the shale analysis log. The water content $w_a$ of the shale (expressed as kilograms of water per kilogram of dry shale matrix) is normalized to the CEC of the shale (moles of monovalent exchange sites in the shale per kilogram of dry shale matrix) by dividing $w_a$ by the CEC to give $A^{-1}$, the water content of the shale per unit of exchange capacity. The variation of $A^{-1}$ with Z is the corrected compaction log for the shale formation which depends only on the type of cations in the shale and the conditions of compaction.

The corrected compaction log shows the corrected water content of the shale as a function of vertical depth. For normal compaction where there is no significant change in the ionic composition of the shale, the quantity $A^{-1}$ will decrease monotonically with Z. The two principal causes of a change in $A^{-1}$ at a given depth are a change in the shale's ability to lose water (and ions) by expulsion and a significant change in the ionic composition of the shale. The ionic composition of the shale is measured and displayed on the cuttings analysis log (FIG. 7), and therefore correlation between cation content and $A^{-1}$ can be made. The remaining cause of a deviation in the compaction trend, the state of compaction of the shale, can therefore be identified. For the case of an undercompacted shale, the value of $A^{-1}$ is higher than expected at a given value of Z.

The state of compaction of the shale, as measured by the parameters $\bar{x}_a$ and A, can be further described by correlation of A with its total sorbed salt (ie, anion) content. For a 1:1 salt such as sodium chloride, the simple Donnan equilibrium (which assumes equality of the activity coefficient of the salt in the shale and the external reservoir) relates the molal chloride concentration $\bar{m}_{Cl}$ in the shale to the equivalent concentration $m_{Cl}$ in the reservoir by $$2\bar{m}_{Cl} = -A + (A^2 + 4m_{Cl}^2)^{1/2} \qquad (25)$$

Figure 10:
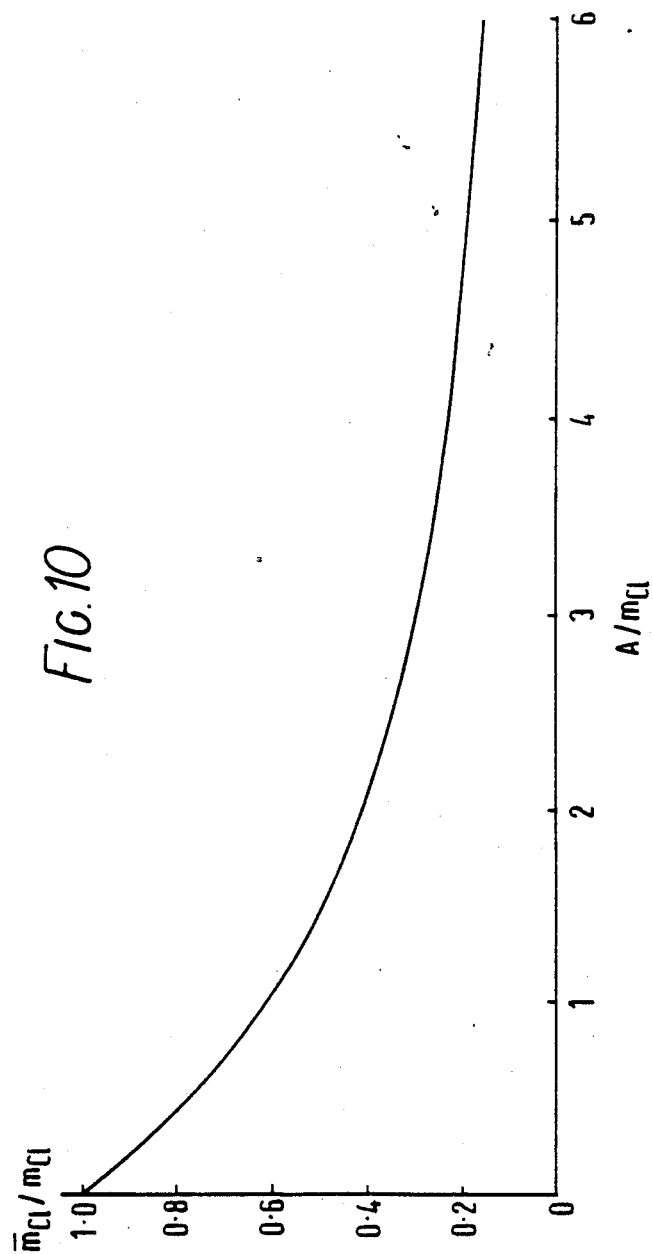
FIG. 10 is a plot of the ratio of the molal chloride concentrations $m_{cl}$ in the shale over the equivalent concentration $m_{cl}$ in the reservoir, against the ratio of the effective concentration A of cation exchange sites over the molal chloride concentration $m_{cl}$ in the reservoir.

The Donnan equilibrium as described by eqn (25) is a salt exclusion equilibrium since for a given value of $m_{Cl}$, the salt content of the shale membrane decreases as the effective concentration of its ion exchange sites increases. If the shale section is characterized by a constant value of the salinity of the solution in the external reservoir, then the anion concentration in the shale is directly related to $\bar{w}_a$ and the CEC. A plot of $\bar{m}_{Cl}/m_{Cl}$ against $A/m_{Cl}$ is shown in FIG. 10 which emphasizes the unique relationship between $\bar{m}_{Cl}$ and A at fixed $m_{Cl}$. The measured anion content of the shale as a function of depth will therefore supplement the compaction trend as represented by the $\bar{w}_a - Z$ and $A^{-1} - Z$ plots.

The "mud advisor" system can calculate the total charge $\bar{C}_a^s$ of the anions (moles of monovalent charge per kilogram of dry shale matrix) in the shale, defined by $$\bar{C}_a^s = \Sigma_a \bar{m}_i Z_i, \qquad (26)$$

from each shale cutting analysis. The total anion charge, which is generally dominated by the presence of the chloride ion, is displayed after each analysis, showing its variation with depth.

The "mud advisor" system constructs a cross-plot of $\bar{C}_a^s$ against A to analyze the compaction trend in the shale as measured by both the normalized water content ($A^{-1}$) and the salt content of the shale. At each datum point, the total anion charge $C_a^s$ of the external reservoir is calculated using eqn (25) to check the consistency of the assumptions.

The shale analysis log also provides important information on the type and quantity of cations which are available for exchange with cations in the mud system. During the drilling of a significant shale formation, the corrected changes in the cation content of the mud filtrate, computed and displayed by the "mud advisor" system, indicate the extent of the interaction (principally cation exchange) between the mud and shale. The "mud advisor" system correlates the measurement of the total cation content of the shale to the measured changes in the cation content of the mud filtrate.

EXAMPLE OF AN ANALYSIS

An example of an analysis embodying the present invention is now given.

The analysis was not conducted at rigsite. Mud samples were taken during off-shore drilling as detailed below, and were subsequently analyzed on-shore by the ion chromatography system, with no prior knowledge of or control over changes in the mud composition during operation. Nonetheless the example does illustrate application of the analysis system and indicate how useful it can be when employed at rigsite concurrently with drilling.

Example Mud System

The mud system to drill the 31 centimetre hole was essentially a bentonite/seawater system with no specific inhibitor (polymeric or ionic) added to control shale sections. Table 1 shows the mud formulation and the function of each mud product.

TABLE 1
Function and Concentration of Mud Products

| MUD PRODUCT | FUNCTION | CONTENT kg per m³ |
|---|---|---|
| bentonite | primary viscosifer | 28–42 |
| XC-polymer | viscosifer | 0.71–1.4 |
| CMC Low-viscosity | fluid loss control | 8.5–11.3 |
| CMC High-viscosity | viscosifer, fluid loss | 1.42–2.84 |
| chrome lignosulphate | dispersant | as required |
| sodium hydroxide | pH control | 2.84–4.25 |
| sodium carbonate | calcium control | 0.85 |
| barite | mud density | as required |

TABLE 2
Formulation of Reference Mud

| MUD PRODUCT | CONCENTRATION (g per liter seawater) |
|---|---|
| bentonite | 35.68 |
| sodium hydroxide | 3.57 |
| sodium carbonate | 0.86 |
| CMC* Low-viscosity | 9.99 |
| CMC High-viscosity | 2.14 |
| XC+ | 1.07 |

*CMC is carboxymethyl cellulose.
+XC is a polysaccharide produced by the action of the plant pathogen xanthomonas campestris (hence XC) on carbohydrates.

With this mud formulation:
the addition of ferrochrome lignosulphonate will be accompanied by a drop in pH, and therefore sodium hydroxide should be added to maintain the pH to the required value;
the solids content of the mud must be kept below 8% by volume by making maximum use of the solids control equipment; when the solids content rises above 8%, mud replacement is recommended (ie, discharge of old mud and replacement by new mud);
the level of excess sulphite in the system is monitored and a sulphite containing oxygen scavenger for corrosion inhibition is added such as to maintain an excess of sulphite of 100–300 ppm;
the carbonate/bicarbonate levels in the mud should be closely monitored; calcium hydroxide (lime) should be added to combat carbonate contamination and maintain the pH in the region 9–10 and the calcium concentration in the region 250–600 ppm.

The mud formulation shown in Table 1 enables a reference mud composition to be defined such that all subsequent compositions (ie, the actual mud samples) can be compared with it. The reference mud is formulated such that the concentration of each product is approximately at the mid point of the range shown in Table 1.

Mud Sample Recovery

Mud samples were taken from three points in the mud flow system; the flow line immediately above the shale shaker, the mud flow immediately below the shaker and from the active (suction) tank.

Each mud sample was placed and sealed in a small 60 ml polythene sample bottle such that the mud completely filled the bottle. Care was taken to ensure that no air space was present in the sample bottle thus minimizing the reduction in pH caused by the absorption of carbon dioxide from the air.

Mud Volumes, Flow Rates, Lag Times and Depth-Time Data

In attempting to quantify mud-formation interactions by the variation of the measured filtrate composition with the time of sampling at the surface, it is necessary to know the time that the mud has spent in the annulus, ie, the mud lag time. A knowledge of the mud lag time enables the mud sample time to be related to the drilled depth when that element of mud entered the annulus. The shortest time in which any chemical information can reach the surface about a change in composition due to the exposure of the new formation is the mud lag time.

The lag time $t_L$ is calculated from $$t_L = \frac{V_A}{v}, \tag{27}$$

where $V_A$ is the total calculated annulus volume and $v$ is the measured mud flow rate. The annulus volume $V_A$ is calculated from the difference between the total hole volume (cased and open hole) and the volume of the drill pipe and bottom hole assembly. It is implicitly assumed in calculating the open hole volume that the hole is in gauge; no actual lag time, using for example the acetylene lag test or other tracer, were measured.

Drilling data provided information on total hole, annulus and pipe volumes. At the start of the sampling:
drilled depth=2181 m
total hole volume=167 m³
annulus volume=137 m³
pipe displacement=11.5 m³
pipe capacity=18.3 m³

The range of flow rates encountered during the sampling was 2.4 to 2.65 m³/min although from 7.13 to 8.72 hours the drilling stopped and mud was circulated at a reduced flow rate of 1.4 m³/min. The mud flow rate at the start of the sampling was 2.6 m³/min giving a lag time of 52.4 min. At the termination of the sampling:
drilled depth=2368 m
total hole volume=181 m³
annulus volume=149 m³
pipe displacement=13.2 m³
pipe capacity=19.1 m³

The final low rate was 2.4 m³/min which gave a lag time of 60.4 min. The lag time during actual drilling ranged from 52.2 to 60.4 minutes over the range of drilled depth 2182 to 2368 m; the lowest calculated lag time occurred during the stoppage in the drilling, although mud circulation continued at the reduced flow rate of 1.4 m³/min, giving a lag time of 97 min. The mud flow rate was calculated from the measured stroke rate and the known capacity of the mud pump (12 litres per stroke).

Figure 11:
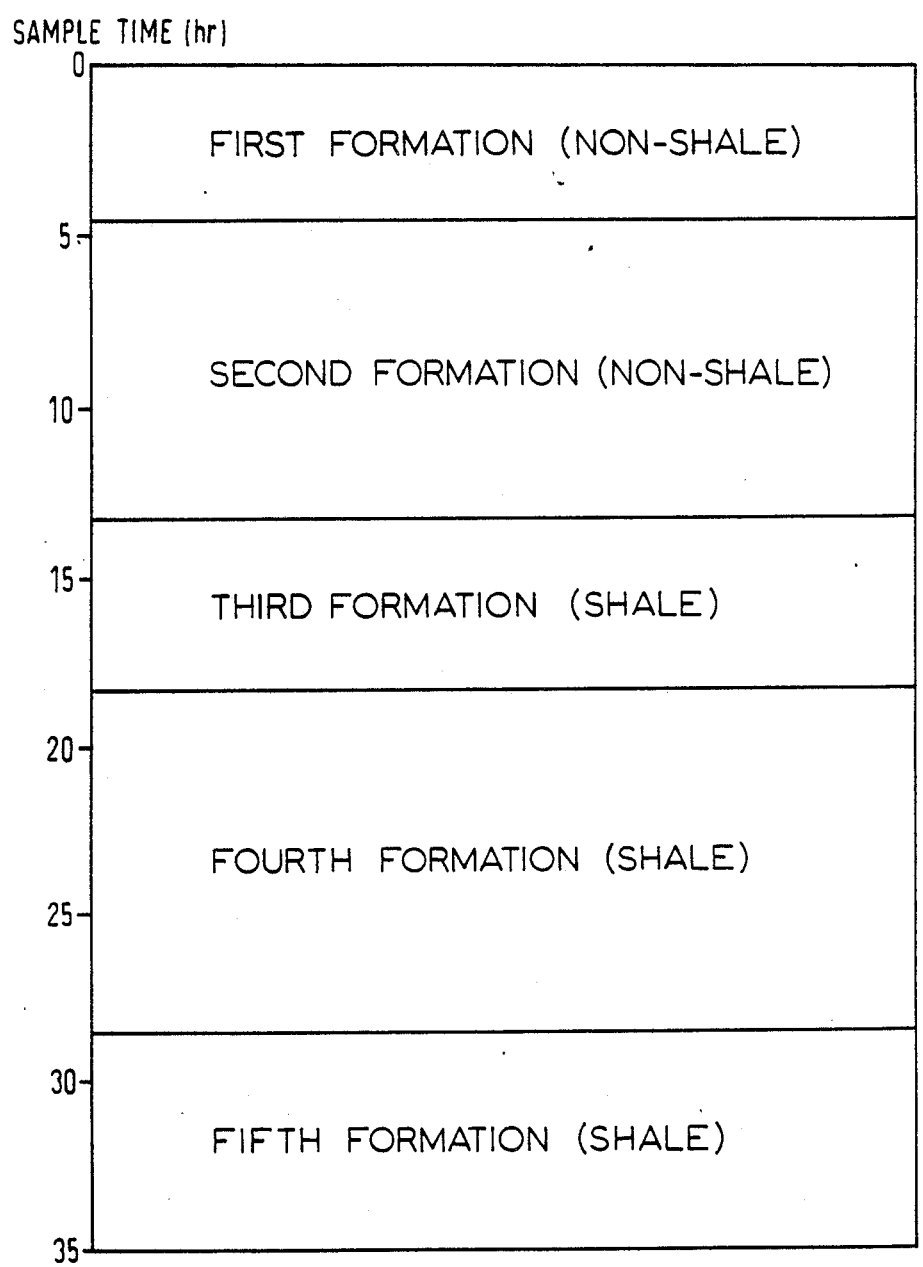
FIG. 11 shows the drilled lithology as a function of sample time in the given field example.

FIG. 11 shows the drilled lithology as seen at the surface as a function of the time from the start of sampling; the time at surface is the sum of the actual time at which the formation was drilled plus the lag time. For example, the second formation was entered at 3.6 hr after sampling started but any information would only reach the surface after 4.5 hr owing to the 0.9 hr lag time; the top of the second formation is therefore shown in FIG. 11 at a surface time of 4.5 hr.

Figure 12:
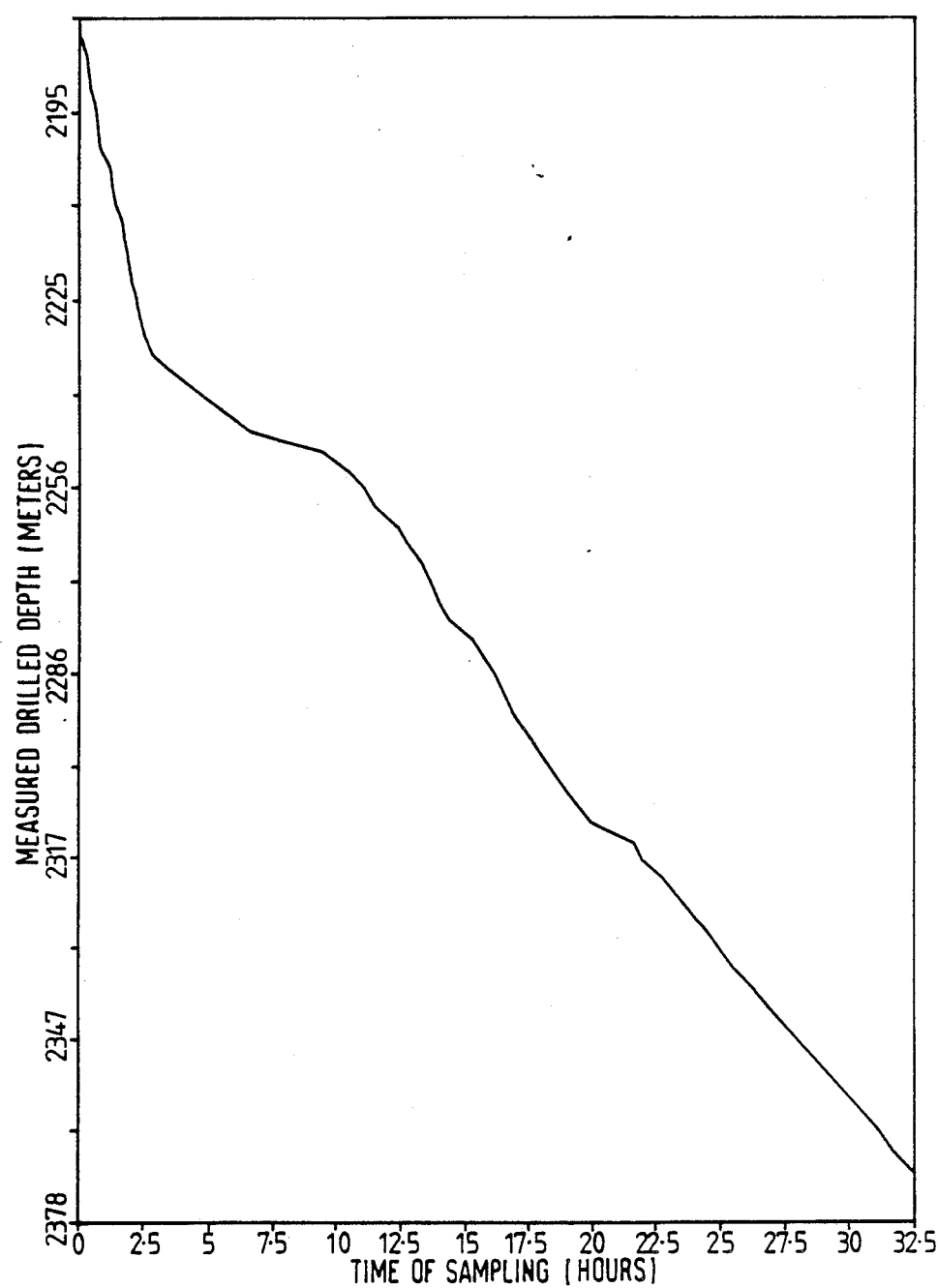
FIG. 12 is the measured drilled depth (in meters) as a function of the sampling time (in hours)

FIG. 12 shows the variation of drilled depth with sampling time. There are two significant breaks in drilling which occur at t=7.1 hr and t=20.3 hr. Sample time can be converted to drilled depth by using FIG. 12.

The Chemical Analysis of Mud Filtrate Samples

Reference Mud Formulation

Table 2 shows the formulation of the reference mud based on the proposed formulation summarized in Table 1. The mud is seawater based, and therefore the ionic composition of the mud will reflect both the salt content of the mud products and that of the seawater. The ionic composition of the seawater used is given in Table 3.

TABLE 3

| Seawater Composition | |
|---|---|
| ION | Cl (molar) |
| Na⁺ | 0.455 |
| K⁺ | 0.010 |
| Mg²⁺ | 0.056 |
| Ca²⁺ | 0.011 |
| Cl⁻ | 0.539 |
| SO₄²⁻ | 0.030 |
| HCO₃⁻ | not measured |
| ε | +0.001 |

ε = Δd, as given by eqn (19)
Cl: concentration

The measured pH of the seawater, in equilibrium with the carbon dioxide in the atmosphere at 25° C., was 8.21. The charge summation of the ions measured by the ion chromatography system, together with the hydroxide concentration as measured by the pH from equation (18) is shown in Table 3. There appears to be a deficit of anions in the seawater sample with an equivalent charge of 0.001 molar. This anion charge is probably attributable to the presence of carbonate and bicarbonate ions in the seawater which cannot be directly measured on the ion chromatography system as normally used. The value of 0.001 molar on the summation of the measured ionic charge in the seawater would be within the accumulative error on each of the analyses. This is a calculated value of apparent carbonate/bicarbonate concentration.

The reference mud is made up to the specification given in Table 2, noting that the mud products are shown in terms of weight per unit volume of seawater. The mud samples were centrifuged using a bench top centrifuge. The chemical composition of the mud filtrate samples was then analyzed using an ion chromatography system.

TABLE 4

| Comparison of Reference Mud Filtrate Composition With Measured Composition of Seawater. | | | |
|---|---|---|---|
| ION | REF MUD (molar) | SEAWATER (molar) | dC (molar) |
| Na⁺ | 0.719 | 0.455 | +0.264 |
| K⁺ | 0.013 | 0.010 | +0.003 |
| Mg²⁺ | 0.030 | 0.056 | −0.026 |
| Ca²⁺ | 0.012 | 0.011 | +0.001 |
| Cl⁻ | 0.667 | 0.539 | +0.128 |
| SO₄²⁻ | 0.032 | 0.030 | +0.002 |
| ε | +0.085 | +0.001 | +0.084 |

The chemical analysis of the reference mud filtrate is shown in Table 4. A comparison between the analyses of seawater and the reference filtrate (Table 4) shows the change in composition due to the addition of the mud chemicals. The change in the concentration dC for each ionic species and the change in pH is also shown in Table 4. The only ionic additions made to the mud system as mud products (see Table 4) are sodium hydroxide and sodium carbonate such that the ion chromatography system should only detect a change in the sodium concentration in the mud system. The increase in the sodium concentration should be 0.105 molar (0.16 molar from sodium carbonate and 0.089 molar from sodium hydroxide). However the measured change in the sodium concentration is 0.264 molar, indicating that a sodium concentration of 0.159 molar is present in the remaining mud additives, ie, bentonite and the polymers.

The addition of the mud products, listed in Table 2, to the seawater has changed all of the ionic concentrations; with the exception of magnesium all of the ionic concentrations have increased. A brief analysis is now given to explain these concentration changes.

The addition of 0.089 moles of hydroxide (in the form of sodium hydroxide) to one litre of nearly neutral seawater should, from eqn (18), raise the pH to 12.95. The measured pH of the mud filtrate is only 9.77 such that the hydroxide concentration in solution is only $6 \times 10^{-5}$ molar; clearly virtually all of the added hydroxide has been removed from the filtrate. The decrease in the magnesium concentration between seawater and mud filtrate is due to the formation of insoluble magnesium hydroxide; the chemical reaction is $$Mh(OH)_2 + 2H^+ = Mg^{2+} + 2H_2O, \qquad (28)$$

and the chemical equilibrium at 25° C. is governed by equation (23).

When the pH is 12.95, the equilibrium magnesium concentration is less than $10^{-9}$ molar, while at a pH value of 9.77, the magnesium concentration is $2 \times 10^{-3}$ molar. The change in hydroxide ion concentration, from the difference between the added hydroxide concentration and the measured pH of the mud filtrate, is 0.089 moles while the change in magnesium concentration is only 0.053 equivalents per litre (ie, 0.053 moles of monovalent charge per litre). No other cation has been lost from solution in this concentration and therefore 0.036 moles of hydroxide ion per litre of mud filtrate have been replaced in solution by another anion which cannot be directly identified by the ion chromatography system. The measured magnesium concentration in the mud filtrate is 0.030 molar which is an order of magnitude higher than the expected value at a pH of 9.77. Thus it appears that there is at least a second reaction (or component) in solution which is removing hydroxide ions and enabling a higher equilibrium magnesium concentration to remain in solution in the filtrate than expected at this pH value (eqn (23)).

The apparent anion deficit in the reference mud filtrate has risen significantly to a value of 0.085 equivalents per litre from the value of 0.001 equivalents per litre in the seawater. The contribution of the added carbonate (added as sodium carbonate) to this imbalance is only 0.016 equivalents per litre, and therefore 0.069 equivalents per litre of anion deficit remains. This anion deficit contains the 0.036 equivalents per litre of anion which is formed from the hydroxide ion, and therefore 0.033 equivalents per litre of deficit was added with the bentonite and/or polymers (Table 2).

The relatively large difference in the sodium ion concentration between the seawater and the mud filtrate (0.264–0.105 molar) is comparable to the corresponding difference in the chloride ion concentrations (0.128 molar), and therefore most of the sodium occurring as a contaminant in the polymers and bentonite is in the form of sodium chloride. The remaining sodium concentration (0.031 molar) must therefore have been largely added as a salt whose anion is not detected by the ion chromatography system since there has been no comparable change in the sulphate ion concentration, the only other anion of significant concentration which is measured. The 0.031 equivalents per litre of sodium correlates well with the 0.033 anion deficit.

The only other inorganic anions of any significant concentration in the mud filtrate are carbonate and bicarbonate ions, although with normal use of the anion chromatography system these ions cannot be directly detected. It is known that sodium carbonate may occur in significant quantities in bentonites used in drilling muds. For example, in the bentonite sample used to prepare the reference mud, the free sodium carbonate content using a seawater wash is 0.014 g/g dry bentonite as sold ($0.3 \times 10^{-3}$ moles of sodium per gram). Thus the reference mud filtrate should contain 0.011 moles of sodium per litre, released by washing 35.68 g bentonite per litre of seawater. Sodium carbonate is commonly used as an extender for bentonite, particularly with regard to its rheological properties. The sodium carbonate in the bentonite may also be present as a result of inadequate washing after the ion exchange process which is used to convert naturally-occurring calcium montmorillonite to the sodium form.

The apparent loss of 0.036 molar concentration of hydroxide ions is balanced by the remainder of the calculated anion imbalance, and this is likely to be due to carbonate/bicarbonate ions. The equilibrium of the mud filtrate with the atmosphere results in carbon dioxide from the air dissolving in the filtrate some of which forms carbonic acid

$$CO_2 + H_2O = H_2CO_3, \quad (29)$$

which dissociates to form carbonate, bicarbonate and hydrogen ions in solution:

$$H_2CO_3 = H^{3O} + HCO_3^- \quad (30)$$

$$HCO_3^- = H^+ + CO_3^{2-} \quad (31)$$

The dissociation of carbonic acid therefore releases hydrogen ions into solution and lowers the pH. The alkali mud filtrate will absorb carbon dioxide from the atmosphere and lower its pH by effectively replacing hydroxide ions in solution by carbonate and bicarbonate ions. The reduction in the hydroxide ion concentration of the reference mud filtrate by 0.089 molar is therefore due to a combination of the precipitation of insoluble magnesium hydroxide and formation of carbonate and bicarbonate ions in solution.

The high magnesium concentration found in the mud filtrate at a pH value of 9.77 is probably due to the formation of ion pairs between magnesium and carbonate and bicarbonate ions, ie, the species $MgHCO_3^+$ and $MgCO_3$ are formed in solution. The formation of ion pairs in solution is greatly enhanced by the presence of the high electrolyte concentrations found in seawater.

The increase in the concentration of potassium ($3.2 \times 10^{-3}$ molar) and calcium ($0.75 \times 10^{-3}$ molar) in the filtrate solution is probably due to impurity in the mud products. The calcium concentration in both the seawater (439 ppm) and the reference mud filtrate (470 ppm) is well within the calcium concentration recommended in the proposed mud system.

It is possible that there has been ion exchange between the potassium in the filtrate and the calcium from the bentonite. It is known that some bentonite samples have up to 50% of their exchange capacity occupied by calcium ions, although nominally it may be sold as sodium montmorillonite. The presence of such a large fraction of calcium in the bentonite is due to incomplete ion exchange in the conversion of the naturally-occurring calcium montmorillonite to the required sodium form. The industrial ion exchange process also tends to leave relatively large quantities of sodium carbonate in the bentonite (see above). Interestingly, there seems to be little exchange between the sodium in the bentonite and the potassium in solution; this may be due to the large concentration of sodium in solution.

In conclusion, the following differences in the composition of the seawater and filtrate are:
(1) the bulk of the hydroxide added to the mud system to produce a high pH is removed from solution by magnesium hydroxide precipitation and conversion to carbonate/bicarbonate by the uptake of carbon dioxide;
(2) a considerable amount of sodium chloride is added to the mud system as contaminants in the CMC and XC polymers;
(3) sodium carbonate is added to the mud system as a contaminant in the bentonite;
(4) there are small increases in the calcium, potassium and sulphate ion concentrations due to trace impurity in the mud product.

The filtrate composition of a batch of active mud samples (which represent about 25% of the total suite of active muds) is now analyzed for the major anions and cations, together with the pH.

Figure 13:
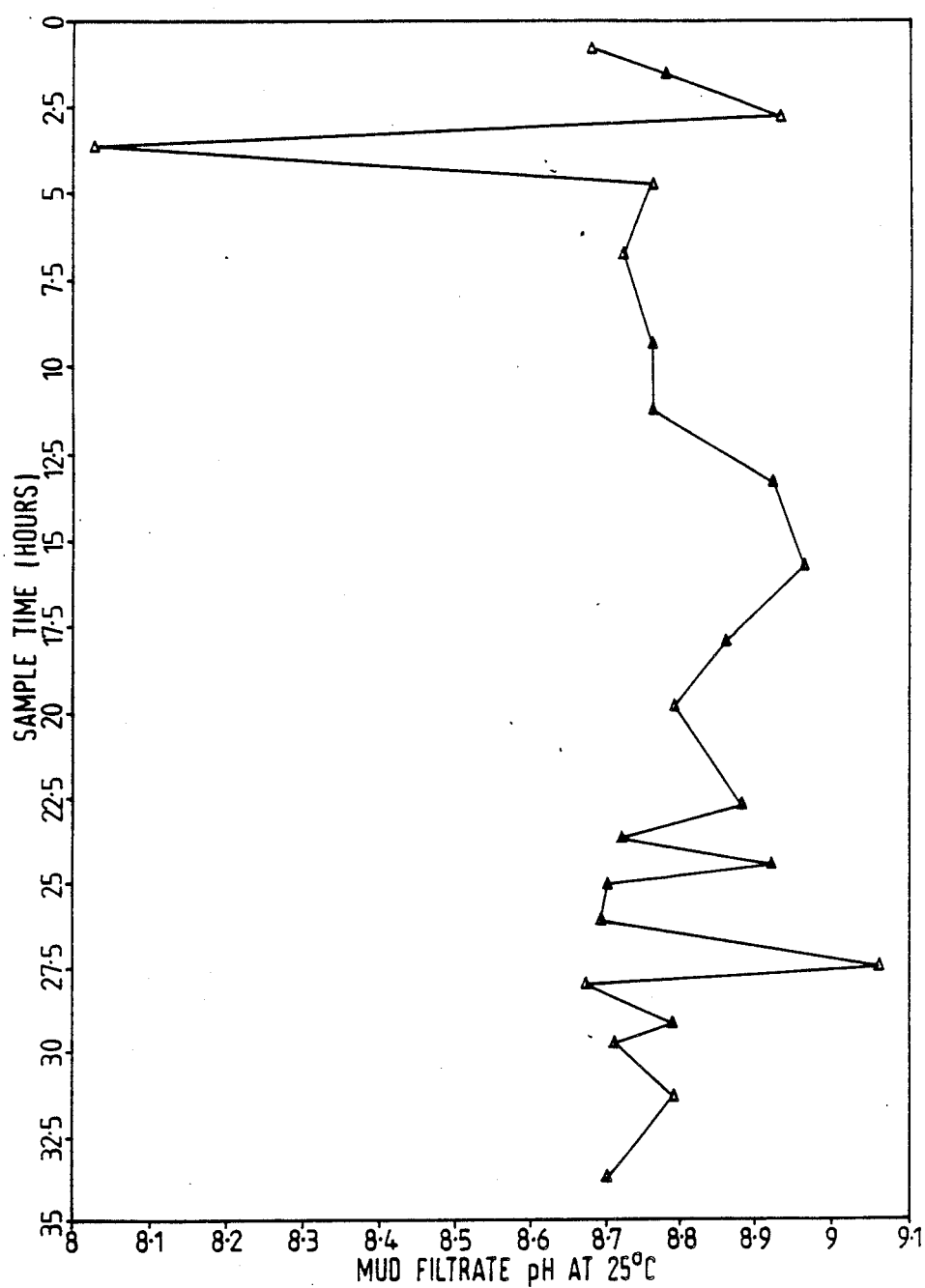
FIG. 13 is a plot of the mud filtrate pH (at 25° C.) versus the sample time.

FIG. 13 shows the variation of the pH of the mud filtrate samples with sample time (in hours). The bulk of the pH values lie in the range 8.7–8.9, with only one mud filtrate sample having a pH value above 9.0. It is apparent that during the sampling period, the pH of the mud system was outside the range of 9–10 stipulated in the engineering recommendations (Table 1), although the exact extent of irreversible pH reduction cannot be estimated. For the first 15 hours, the pH gradually rises (excepting the single outlier at t=3.7 hr), reaching a pH value of almost 9 at t=15 hr. For sample times greater than about 22 hours, the measured pH values of the filtrate samples become rather erratic. It has been shown that the variations of the pH correlate with the variations in the solids content of the mud. The broad trend is that the higher filtrate pH values correlate with the higher solids content.

The Sodium Content of the Mud Filtrate Samples

Figure 14:
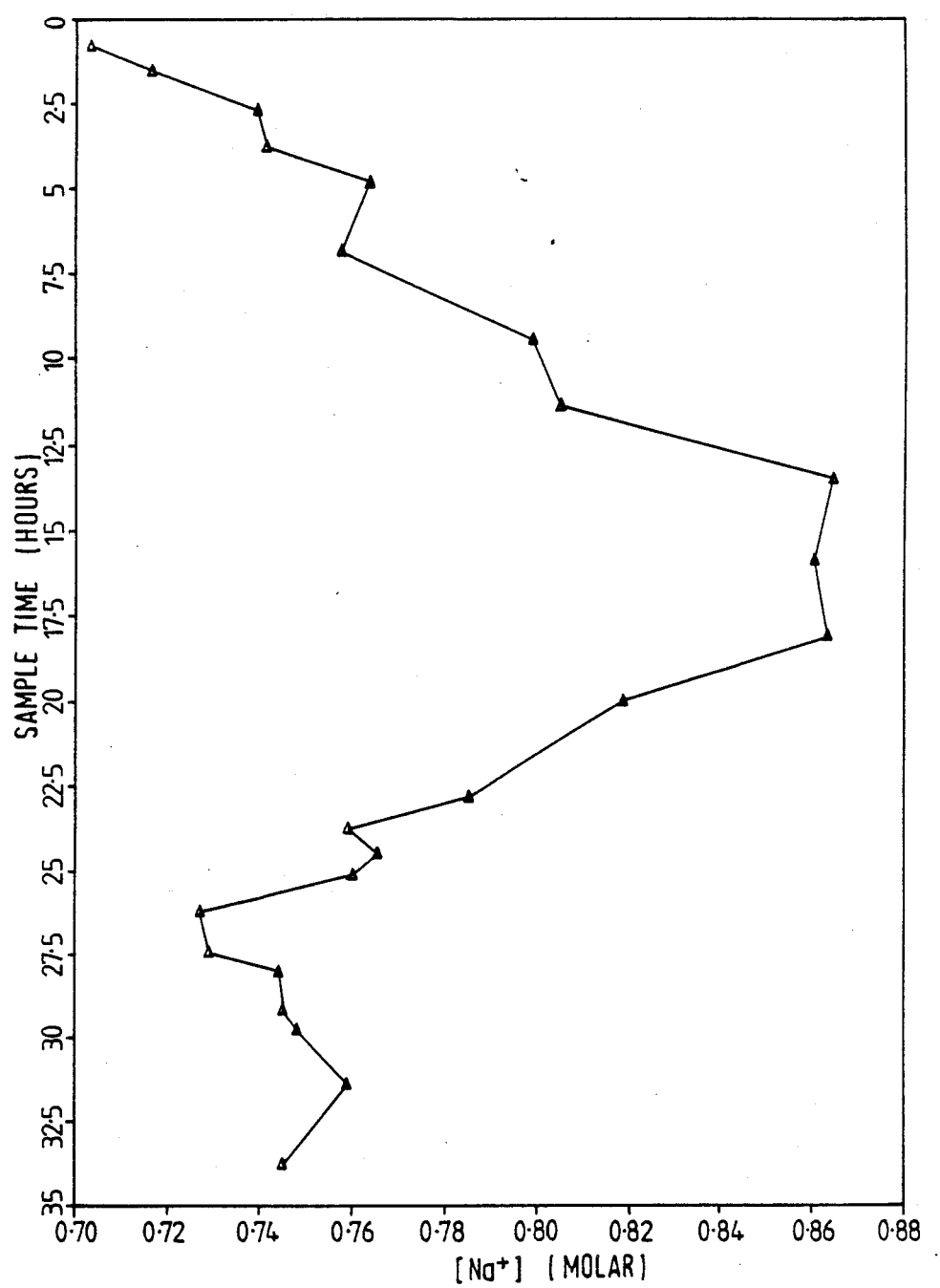
FIGS. 14, 15, 16, 17, 18, 19 show the variations, versus the sample time, of the ion concentrations in sodium, chloride, sodium-chloride, potassium, magnesium and calcium, respectively.

FIG. 14 shows the variation of the sodium concentration in the active mud filtrate samples as a function of sample time. The first 13 hr of the sampling period are characterized by a large increase in the sodium concentration of the filtrate.

The sodium concentration of the reference mud filtrate is 0.719 molar, such that for most of the sampling period the sodium concentration of the samples is significantly above the reference value. The sources of the added sodium are sodium hydroxide for the maintenance of pH, sodium carbonate for the precipitation of calcium carbonate, and sodium carbonate and sodium chloride as impurities in the bentonite and polymers, respectively.

A peak concentration of about 0.86 molar is reached between $t=13$ hr and $t=18$ hr which closely corresponds to the drilling of the third formation (see FIG. 11). The sodium content of the filtrate samples drops sharply after $t=18$ hr and continues to drop reaching a concentration of about 0.73 molar between 26 and 27.5 hr, whereupon the sodium concentration rises and fluctuates about a mean value of about 0.745 molar for the remainder of the sampling.

The decrease in the sodium concentration after $t=18$ hr seems to be attributable to two main causes. Firstly, the partial replacement of the mud system (or even dilution with seawater) will reduce the sodium content of the mud filtrate samples. The duration of mud replacement/dilution and the replacement volume are unknown. The subsequent sharp increase in the solids content is presumably due to cuttings and borehole dispersion. The power cut at $t=20.5$ hr stopped all mud circulation for about 50 minutes, after which time the solids content of the mud had largely returned to its original (ie, pre-replacement) value of about 26.5%. If the mud was being replaced and/or diluted for sample times beyond about 24 hours the measured solids content does not show it other than by the fluctuations in the weight percent solids content (ie, ratio of the weight of solids to the weight of mud) which may indicate non-mixing in the active tank. The possibility of a second mechanism for removing sodium from the mud system is discussed below.

The Chloride Content of the Mud Filtrate Samples

Figure 15:
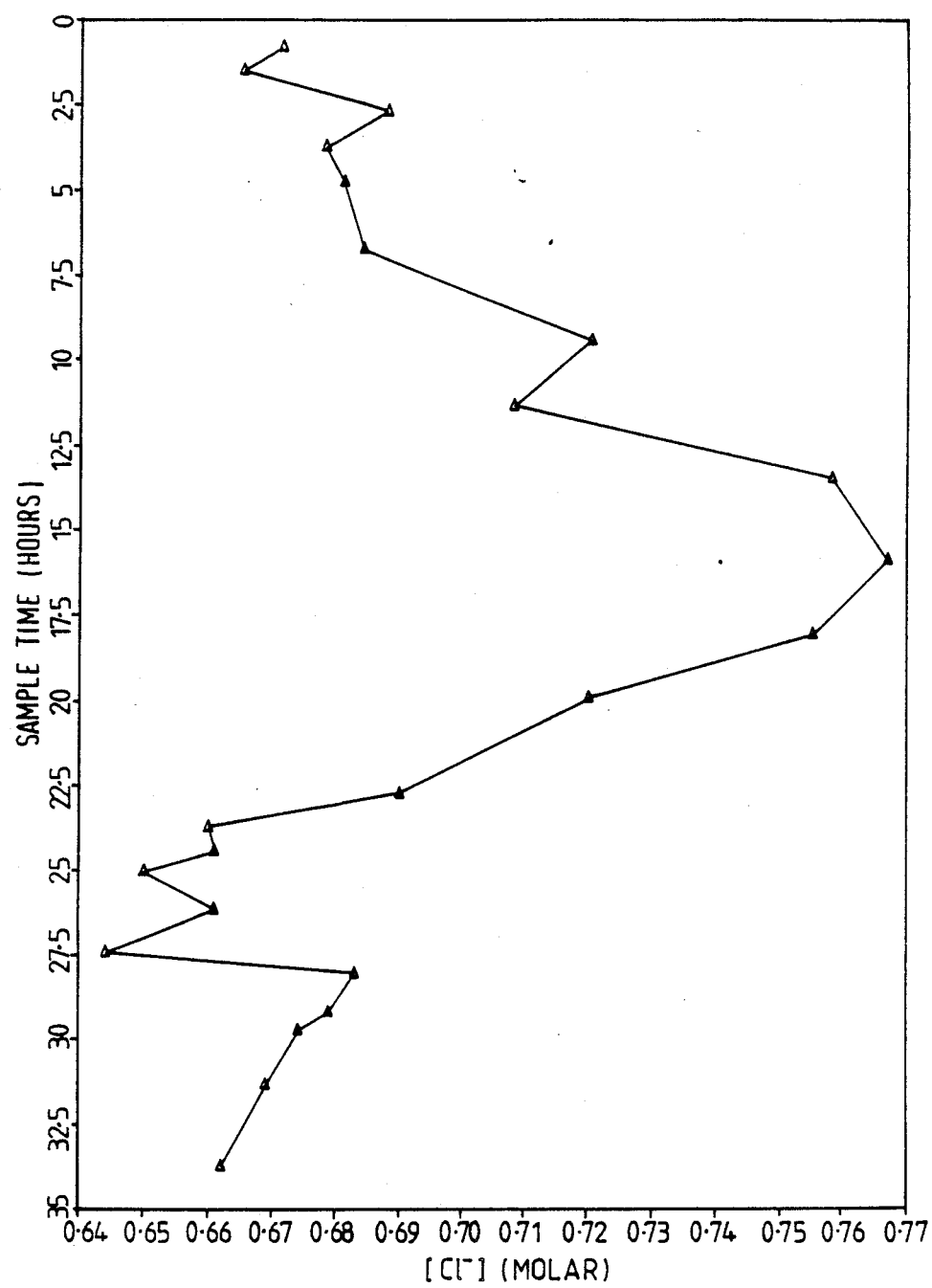
Figure 16:
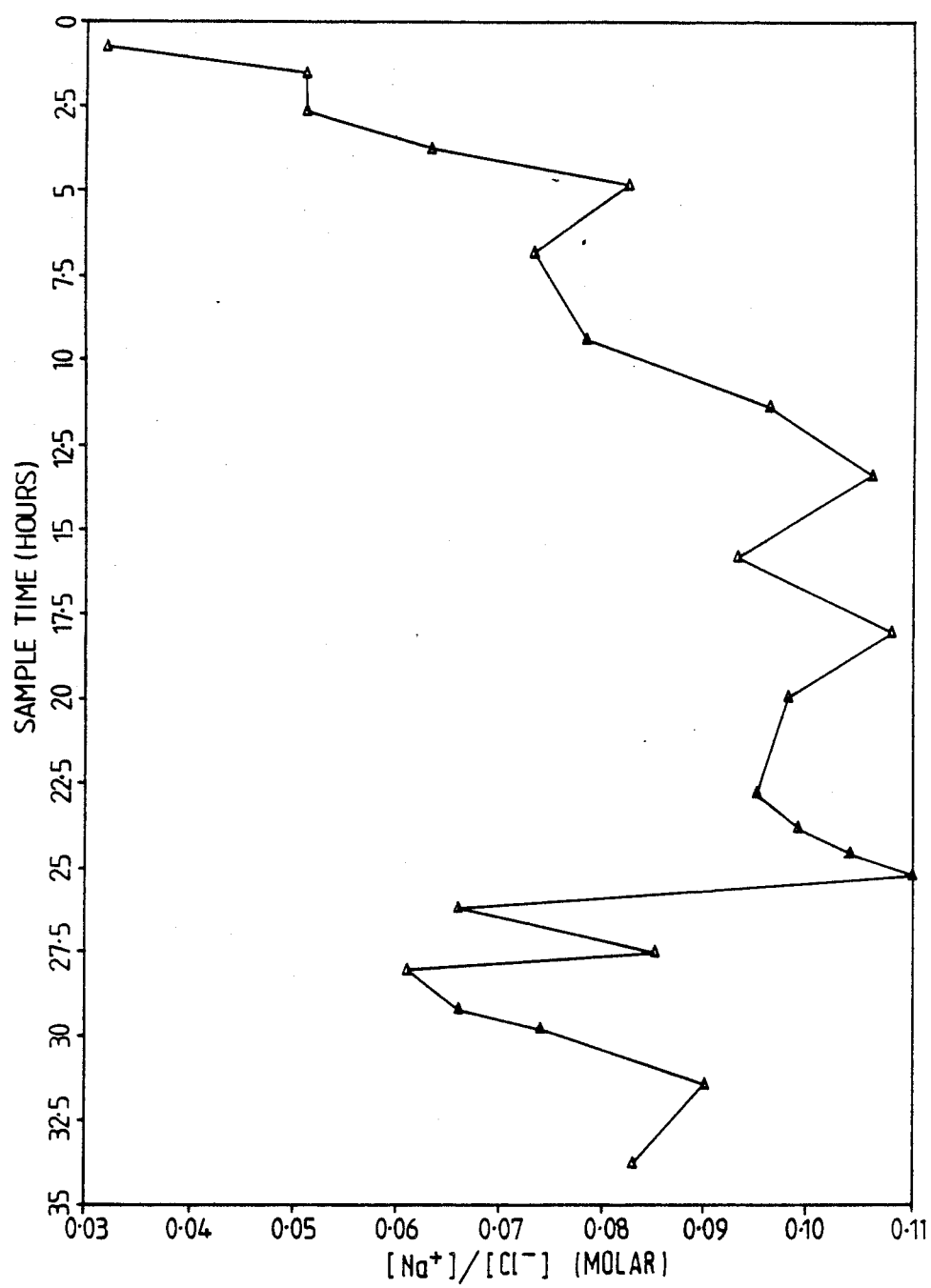

FIG. 15 shows the variation of the chloride ion concentration in the mud filtrate samples with sample time. The trend of the change in chloride ion concentration closely follows the trend in the change of the sodium concentration. However a substantial change in the sodium content of the mud samples is not accompanied by a change in the chloride content, and therefore sodium is being added to the mud system in the form of another salt. The difference between the sodium and chloride ion concentrations is shown in FIG. 16, where it is seen that only about one half of the total increase in sodium ion concentration is due to the addition of sodium chloride. The difference in sodium and chloride ion concentrations is $-0.084$ molar in seawater and $+0.052$ molar in the reference mud filtrate. The most likely anion which is balancing the increase in sodium in the mud system is carbonate or bicarbonate, the pH of the filtrate samples being too low to account for hydroxide concentrations of the order of 0.1 molar (see FIG. 13). The apparent anion deficit in the mud system is discussed in more detail below.

The decrease in the sodium concentration at $t=18$ hr is matched by the decrease in the chloride ion concentration since the difference in their concentrations changes little at this time (see FIG. 16). There is therefore a reduction in the sodium chloride concentration in the mud system, and this removal coincides with entry into the fourth formation (FIG. 11). A second possible mechanism for the reduction of sodium chloride is salt sorption by the cuttings as they swell and begin to disperse in the annulus.

For sample time greater than 25 hr, the filtrate samples become enriched in chloride relative to the sodium content. This enrichment suggests that there is either the addition of another chloride salt or the removal of a sodium salt other than sodium chloride, or a discharge of the mud system and replacement with mud whose composition more closely resembles that of the reference mud.

The Potassium Content of Mud Filtrate Samples

Figure 17:
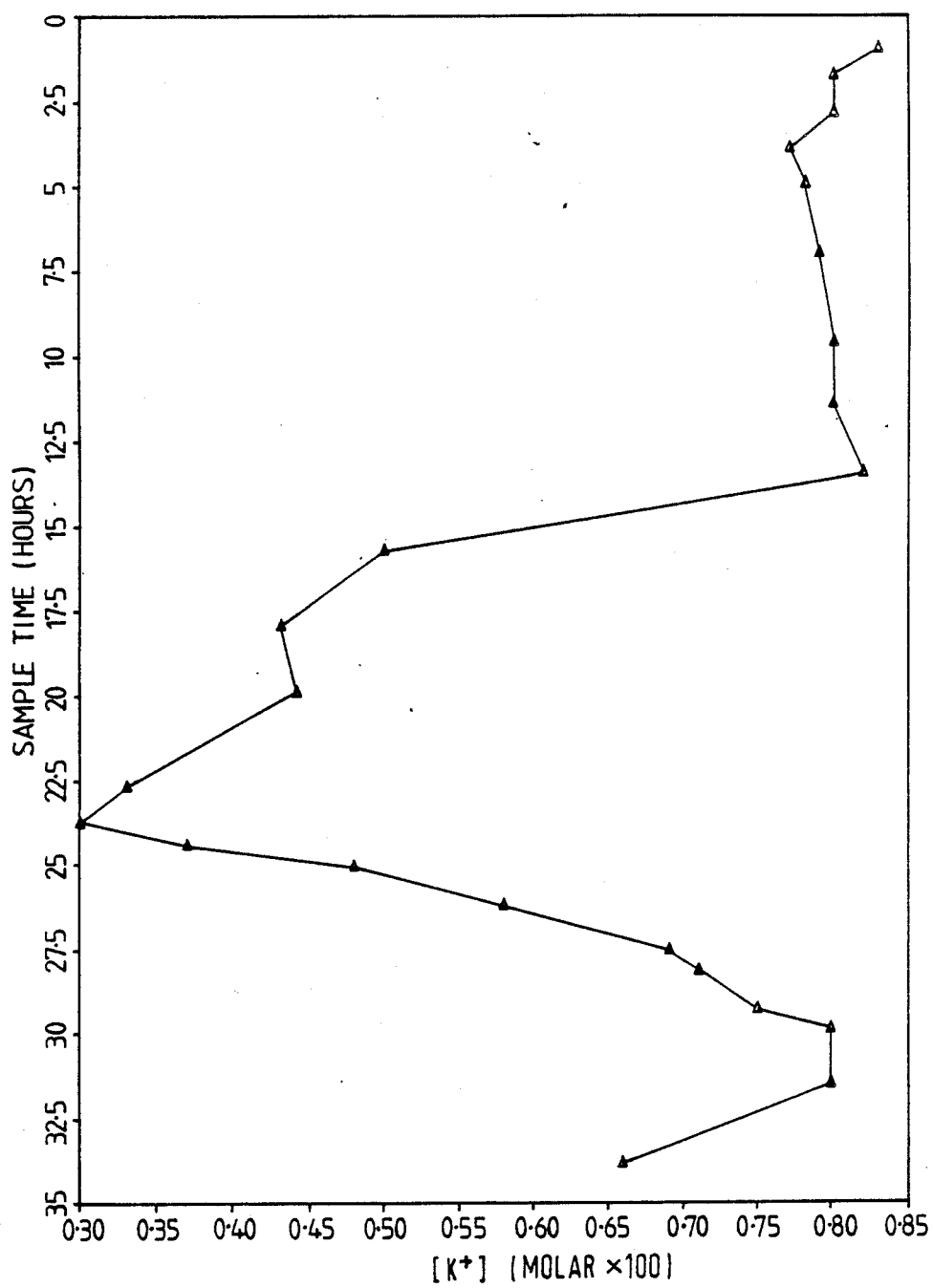

The determination of the potassium content of mud filtrates is an important requirement of any method used to analyze the chemical composition of mud samples. It is stressed that the only source of potassium in the mud system is from seawater (388 ppm or 0.010 molar), since no potassium salts were added to produce an inhibitive mud system. FIG. 17 shows the concentration of potassium in the mud filtrate as a function of sample time. Before $t=13.2$ hr, the potassium content of the filtrate samples is quite constant at about 0.008 molar (310 ppm), close to the value of 0.010 molar found in seawater but below the value of 0.013 molar found in the reference mud filtrate. Beyond $t=13.2$ hr, the potassium concentration drops sharply, reaching a minimum value of 0.003 molar at $t=23.7$ hr. A comparison of FIG. 17 with FIG. 11 shows that the sharp decrease in the potassium content of the filtrate samples almost exactly coincides with the boundary between the second and third formations encountered during the sampling. The third formation is therefore removing potassium from the mud system, either in the form of a salt by salt sorption or by a cation exchange mechanism.

For sample time greater than about 24 hr, the potassium content of the mud filtrate samples starts to increase, and at $t=29.7$ hr returns to the concentrations found for t less than 13.2 hr. Since the principal source of potassium in the mud system is seawater, it can be concluded that a significant addition of seawater to the mud system occurred between about t-24 hr and $t=30$ hr.

The concentration of potassium in the filtrate decreases sharply after $t=31.3$ hr which suggests that by this time the addition of seawater has stopped and there is now removal of potassium by the fifth formation.

The Magnesium Content of the Mud Filtrate Samples

Figure 18:
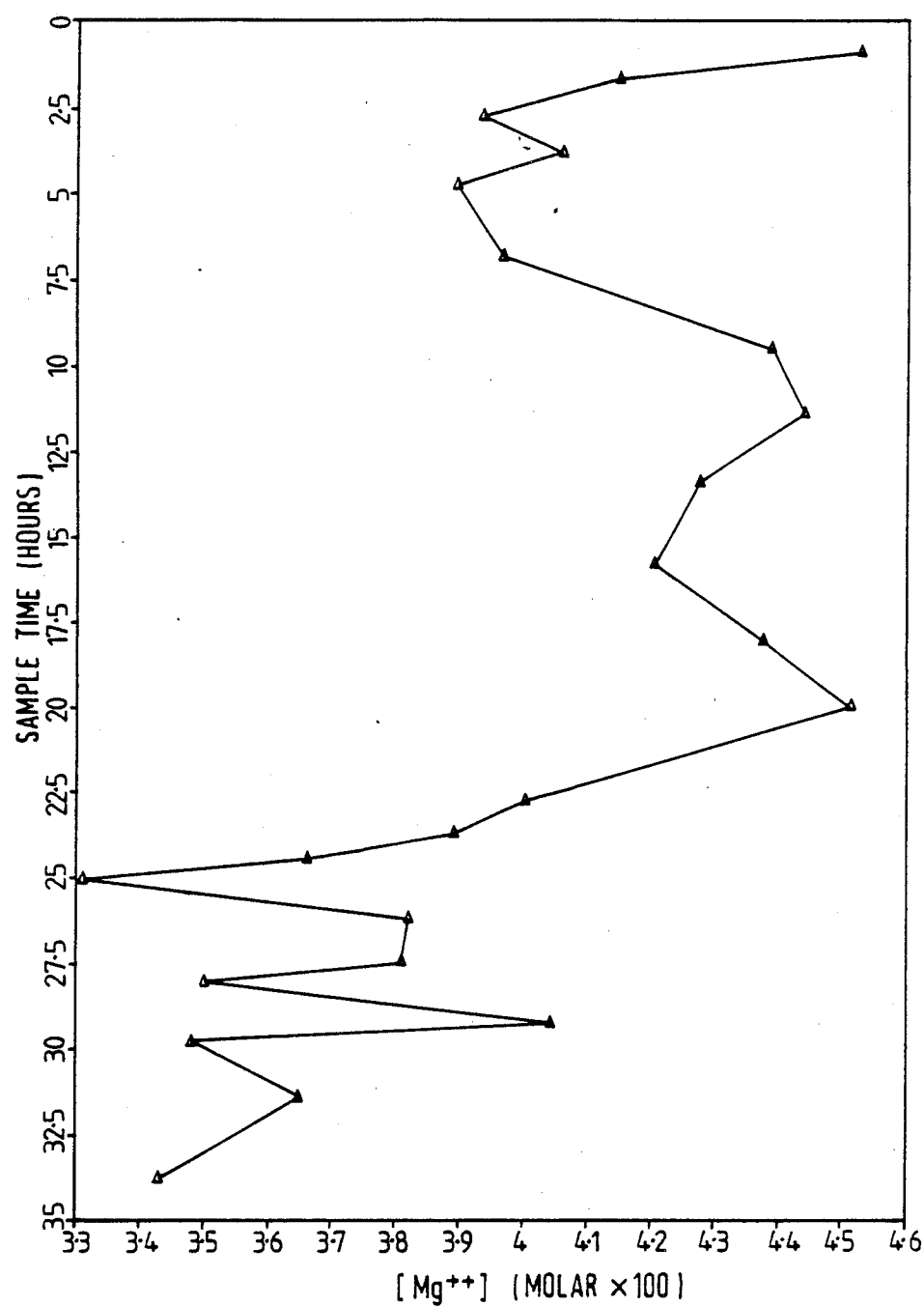

The variation of the magnesium concentration of the mud filtrates with sample time is given in FIG. 18. The only source of magnesium in the mud filtrate samples is from seawater, where the concentration is 0.056 molar (see Table 3); the magnesium concentration in the reference mud filtrate is 0.030 molar. The magnesium concentration in the filtrate samples is therefore always lower than that for seawater but always above that for the reference mud filtrate.

Comparison of FIG. 18 with FIG. 11 shows that the initial decrease in the magnesium content of the filtrate samples corresponds to the first formation, while the following increase in concentration corresponds to the second formation. The addition of seawater to the mud system at t=17 hr appears to reverse a trend (starting at about t=15.5 hr) of decreasing magnesium concentration in the third formation. However at t=22.7 hr the magnesium concentration in the filtrates drops sharply and continues to drop to reach its lowest concentration (0.033 molar) at t=25 hr. This sharp drop occurs shortly after the fourth formation has been penetrated, possibly indicating magnesium sorption or cation exchange between the mud and the formation. An alternative reason for the decrease is the continual addition of fresh mud which has a magnesium concentration significantly below the value for seawater, ie, the pH of the added mud is above the pH of seawater. Some evidence for the addition of high pH mud between t=22.7 hr and t=25.0 hr is the relative enrichment of sodium (compared to chloride, FIG. 16) in the filtrates, which is consistent with the addition of sodium hydroxide to the mud system.

The magnesium concentration rises after t=25.0 hr, although the subsequent variation in the magnesium content is somewhat erratic and rather similar to the behavior found in the pH data (FIG. 13). For example, the magnesium concentration seems to closely mirror-image the filtrate pH with a lag of about 90 mins in the magnesium sample time. Such a relationship is expected from eqn (23), although the cause of the 90 minute lag in the correspondence is unclear.

The Calcium Content of the Mud Filtrate Samples

Figure 19:
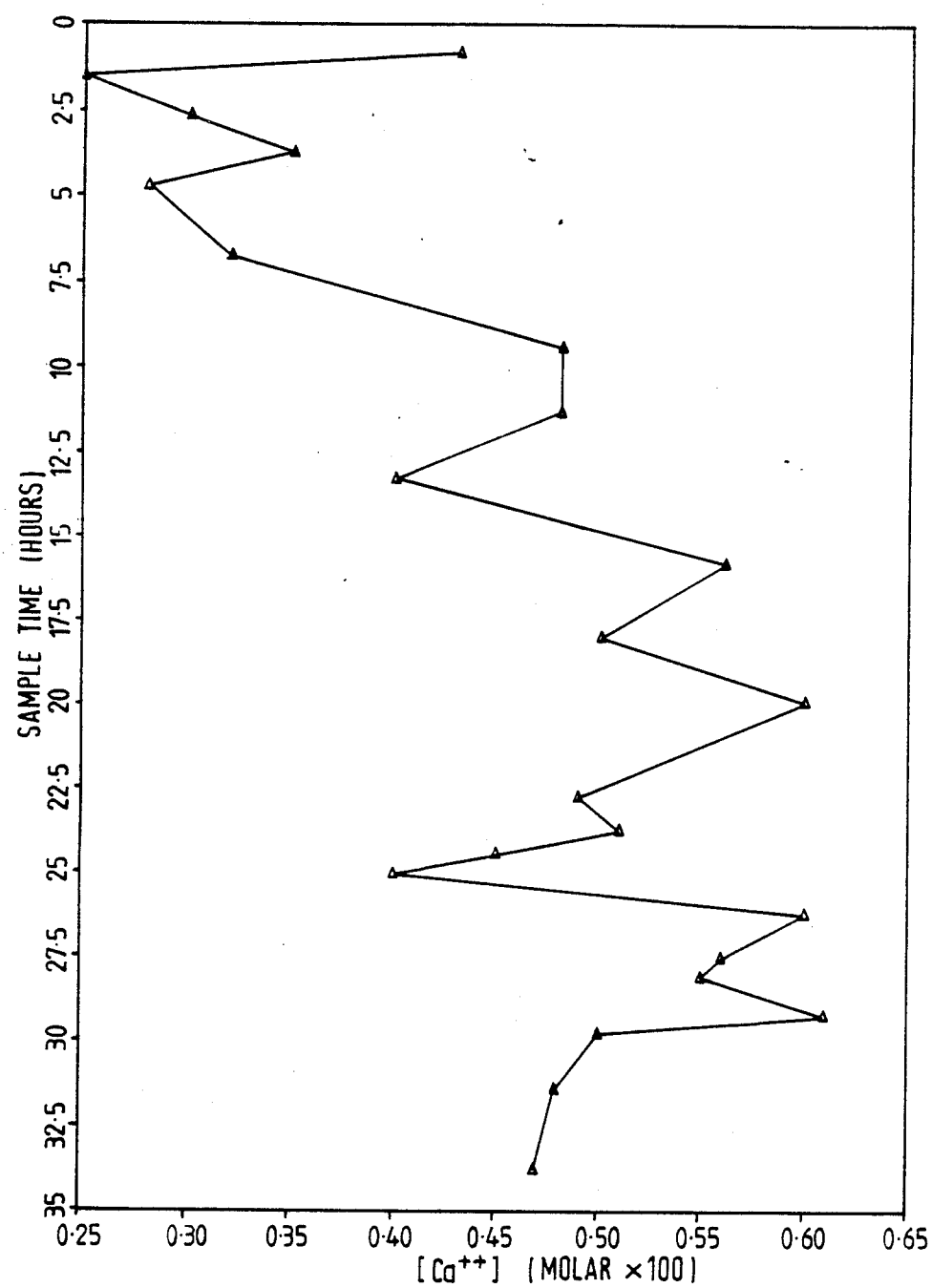

FIG. 19 shows the corresponding variation of the calcium content of the filtrates with sample time. In contrast to the magnesium concentration, the calcium concentration in all of the filtrate samples is well below both that in the seawater (0.011 molar) and the reference filtrate (0.012 molar). The mud specification required that the calcium concentration be maintained in the region 250–600 ppm, while the maximum measured calcium concentration in the filtrate samples is only 242 ppm.

The calcium concentration in the filtrates generally increases from t=0 to t=19.8 hr where it reaches a peak concentration of 0.006 molar, although the trend is not smooth. Beyond t=19.8 hr the calcium concentration decreases until t=25.0 hr whereupon it increases again and achieves the same peak concentration at t=26.2 hr and t=29.1 hr. The final 4.5 hr of sampling are characterized by a decrease in the calcium concentration.

The calcium content of the filtrates broadly follows the magnesium content, the general trend being that both ion concentrations increase and decrease together. There are some exceptions, in particular, in the first formation the magnesium content decreases while the calcium content both decreases and increases. Both ion concentrations show a sharp decrease on entering the fourth formation, followed by a sharp increase due to seawater addition.

Figure 20:
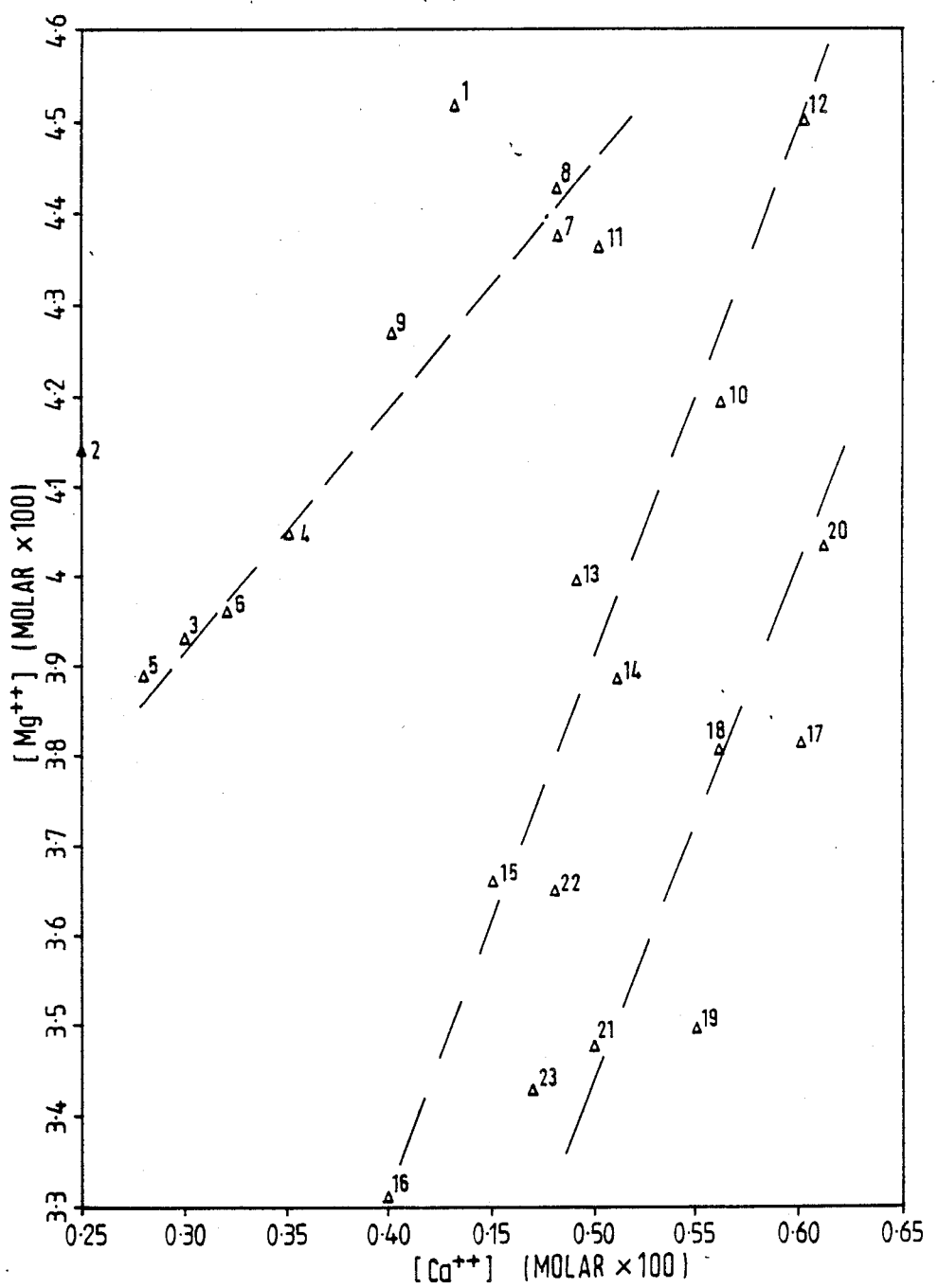
FIG. 20 is a plot of the calcium ion concentration (molar × 100) versus the magnesium ion concentration (molar × 100)

FIG. 20 is a cross-plot of the calcium and magnesium concentrations in the filtrate samples. The points, which are numbered in sequence of increasing time, show two distinct regions. Points 1 to 11 (noting outliers at 2 and 10) represent ionic concentrations in filtrates from the first, second and third formations, while those numbered 12–23 are from the fourth and fifth formations.

The first 11 points give a reasonably linear relationship which is well separated from points 12–23. The latter points seem to form two different but parallel lines composed of points 12–16 and 17–23, respectively. The points 12–16 correspond to the reduction in both the calcium and magnesium concentration on entering the fourth formation, while the points 17–23 correspond to the erratic behavior which seems to result from the addition of seawater. The general trend in the cross-plot is that some formations are characterized by a high magnesium and low calcium content, while the other formations are characterized by a high calcium and low magnesium content. This plot is one of the most sensitive indicators of chemical changes of the mud due to addition of mud products and/or mud-formation interactions. For example, carbonate dissolution or precipitation occurring in the mud are characterized by data on the plot of FIG. 20 collapsing about a straight line passing through the data referenced 3 to 11.

The Sulphate Ion Concentration of the Mud Filtrate Samples

Figure 21:
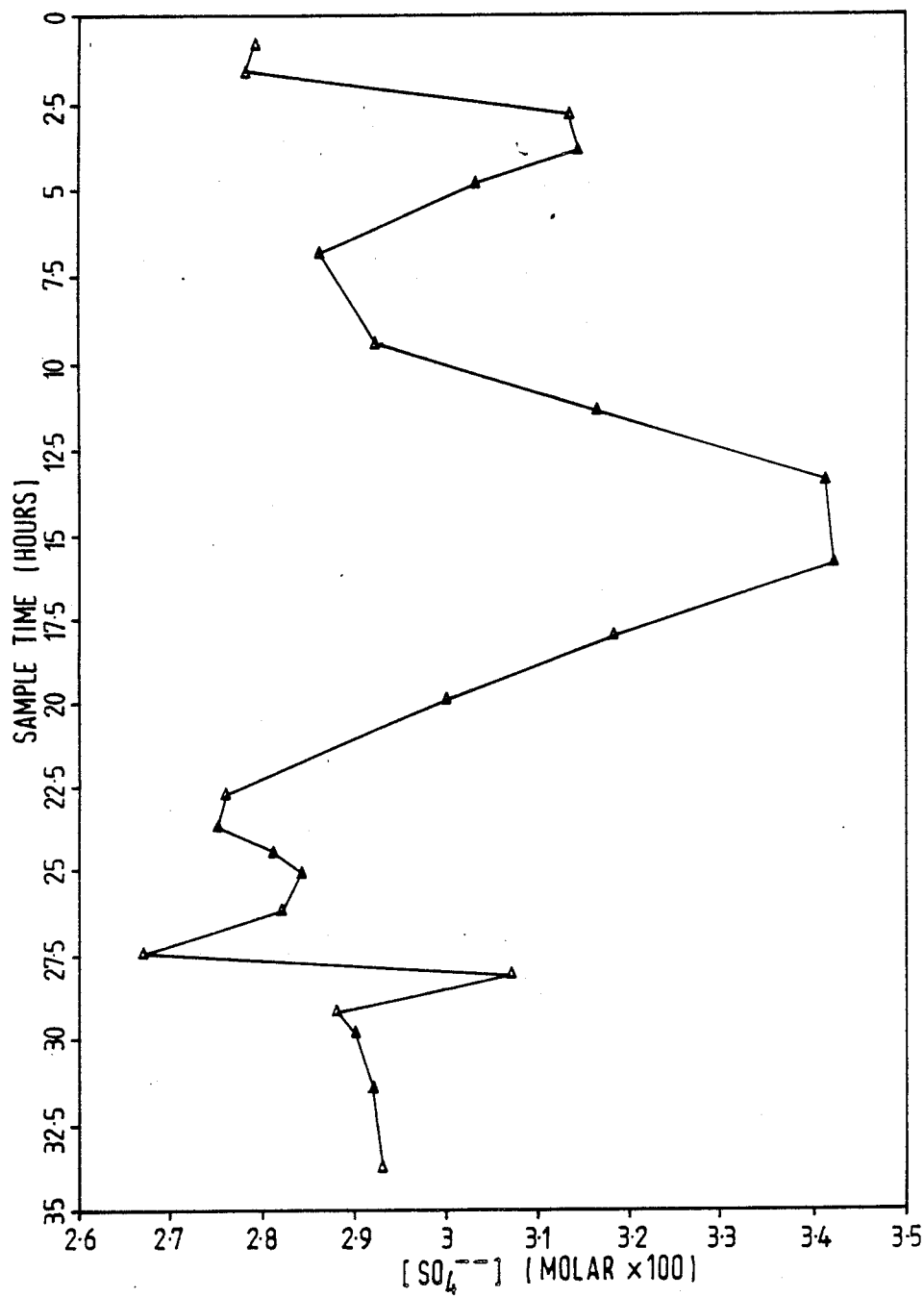
FIG. 21 is the sulfate ion concentration (molar × 100) versus the sample time (in hours)

FIG. 21 shows the variation of the sulphate ion concentration in the mud filtrate samples as a function of time. The concentration of sulphate in the reference mud filtrate is 0.032 molar, of which 0.030 molar comes from seawater. The mud products shown in Table 2 are making a small sulphate addition to the mud system, probably in the form of sodium sulphate. The discussion of pH measurements hereinbefore suggests that there has been some irreversible reduction of sulphate ions by anaerobic bacterial action, and therefore the sulphate levels in the filtrates when measured in the laboratory are likely to be lower than when the mud was sampled at the rig site. This emphasizes again the necessity to perform the analysis directly at the rig site.

The measured sulphate concentration of the mud filtrate samples lies reasonably well in the region of the seawater and reference filtrate concentrations. Two pronounced peaks can be seen between t=2.6 hr and t=6.7 hr, and t=9.3 hr and t=22.7 hr, where the base value of concentration after the second peak achieves the initial sulphate concentration of 0.028 molar. The first peak attains a value of 0.031 molar, while the second peak value is 0.034 molar. With the exception of a concentration dip at t=27.4 hr followed by a sharp peak at t=28.9 hr, the sulphate concentration gradually rises from the base value of 0.028 molar to closely approach the sulphate concentration in seawater.

The increase in the sulphate concentration of the filtrate samples above that of seawater is due to impurities in the added mud products. The presence of the two sulphate peaks shown in FIG. 21 are therefore indicative of the addition of mud products. In both cases the increase in the sulphate concentration is followed by a decrease which is tending to reduce it back to the value of seawater. The reduction in concentration is a consequence of either the mixing of the mud in the annulus or dilution with seawater. The reduction in sulphate concentration after the first peak has been reached, which occurs over the time period t=3.7 hr to t=6.7 hr, does not seem to be due to the addition of seawater since no other ionic species indicates a return to the concentration of seawater. It is likely therefore that this reduction in measured sulphate concentration is due to mixing in the active tank. The reduction in sulphate concentration after the second peak has been reached may be due to seawater addition or mud replacement. The decrease in the sulphate concentration correlates with the large decrease in the sodium and chloride ion concentrations (FIG. 14 and FIG. 15), also indicating that seawater addition occurred at this time.

The sulphate concentration of the filtrate samples correlates well with the sodium concentration, which might be expected since the sulphate is added in the form of sodium sulphate as an impurity in the bentonite and polymer mud products.

The Apparent Anion Deficit in the Filtrate Samples

The summation of the total measured anion and cation charge in each mud filtrate sample shows that there is an apparent anion deficit Ad as given by equation (19). It is stressed that the anion deficit is only apparent and is a measure of the anion species in solution which cannot be measured using the ion chromatography system. The anion deficit includes the pH but this can be measured by other means and taken into account. It is expected that the anion deficit is largely carbonate and bicarbonate ions.

Figure 22:
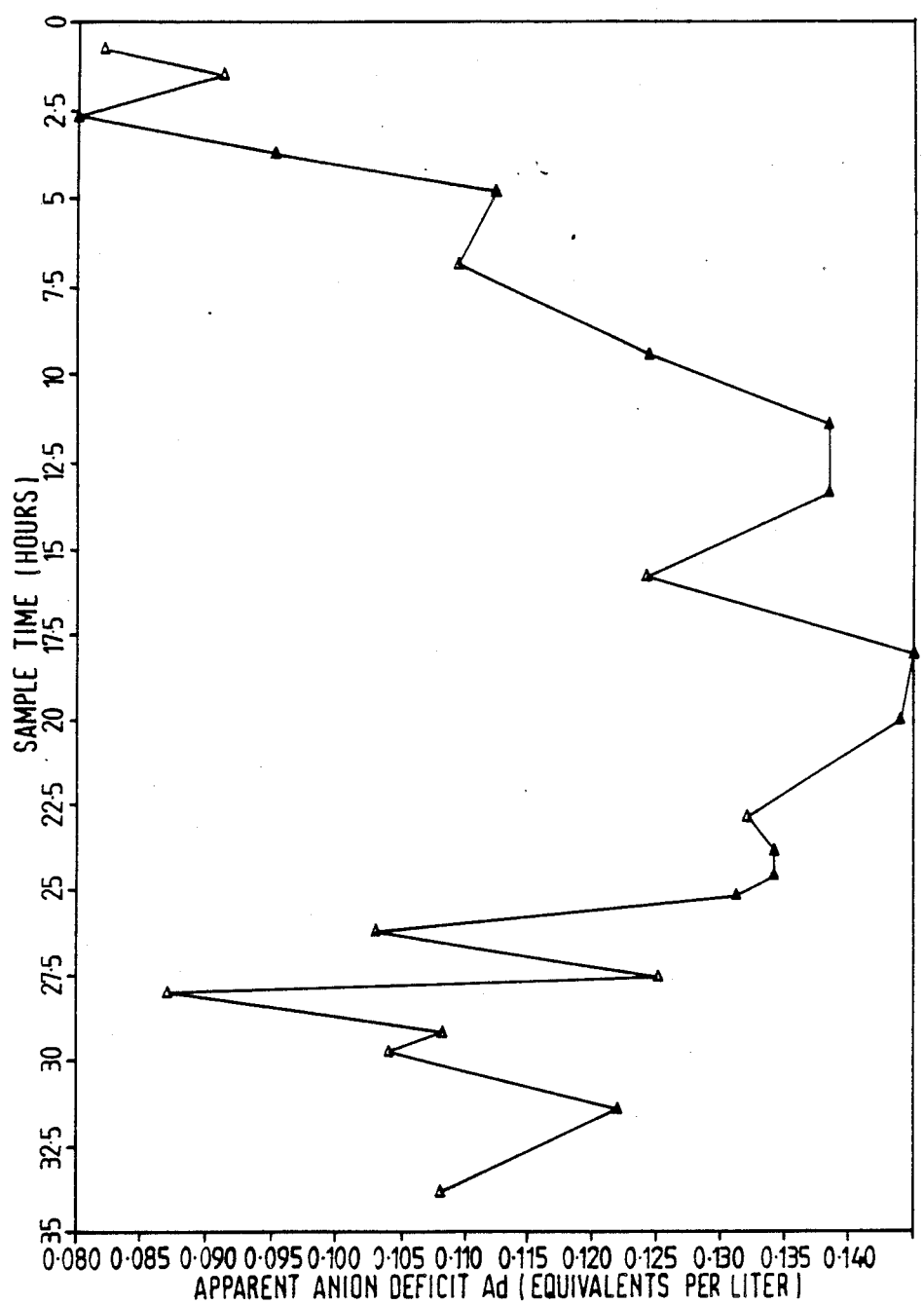
FIGS. 22 and 23 show the apparent anion deficit (equivalents per litre) versus the sample time (in hours) and the sodium-chloride concentration (equivalents in litre), respectively.

FIG. 22 shows the apparent anion deficit (Ad) in the mud filtrate samples as a function of sample time. It is expected that the anion deficit is largely carbonate or bicarbonate which is effectively in the sodium form. A comparison of FIGS. 14 and 22 shows that Ad correlates well with the sodium concentration in the filtrate samples, although there are some significant differences. Firstly, there is a sharp decrease in the sodium ion concentration at $t=18$ hr which is not matched by the anion deficit, particularly between $t=22.5$ hr and $t=25$ hr. Secondly, the behavior after $t=25$ hr is rather erratic, which is also characteristic of the magnesium and calcium ion concentrations.

Figure 23:
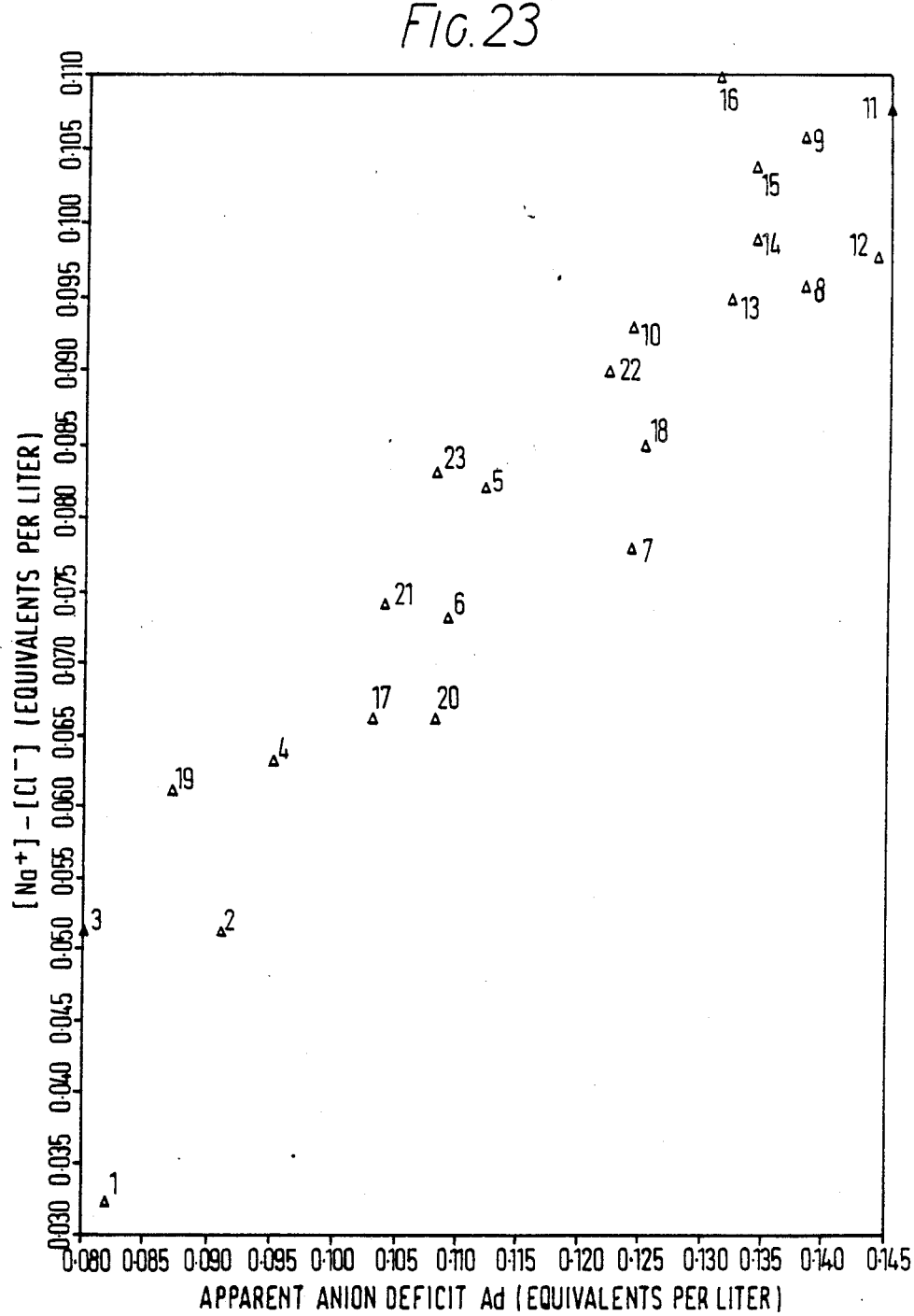

The analysis of the reference mud filtrate showed that the anion deficit could be attributed to carbonate/bicarbonate, and that the balancing cation was almost entirely sodium. The comparison between Ad (FIG. 22) and the (sodium-chloride) ion concentration (FIG. 16) shows rather better agreement between Ad and ([Na]-[Cl]) than Ad and [Na], although in contrast to the reference mud filtrate, Ad is always significantly larger than ([Na]-[Cl]). The carbonate/bicarbonate concentration in the mud samples is therefore larger than the excess sodium, ie, the sodium other than that present as sodium chloride, and thus there is at least a second source of carbonate. A cross-plot of ([Na]-[Cl]) as a function of Ad, FIG. 23, shows a generally linear trend where although the gradient is approximately unity, Ad is always larger than ([Na]-[Cl]).

Figure 24:
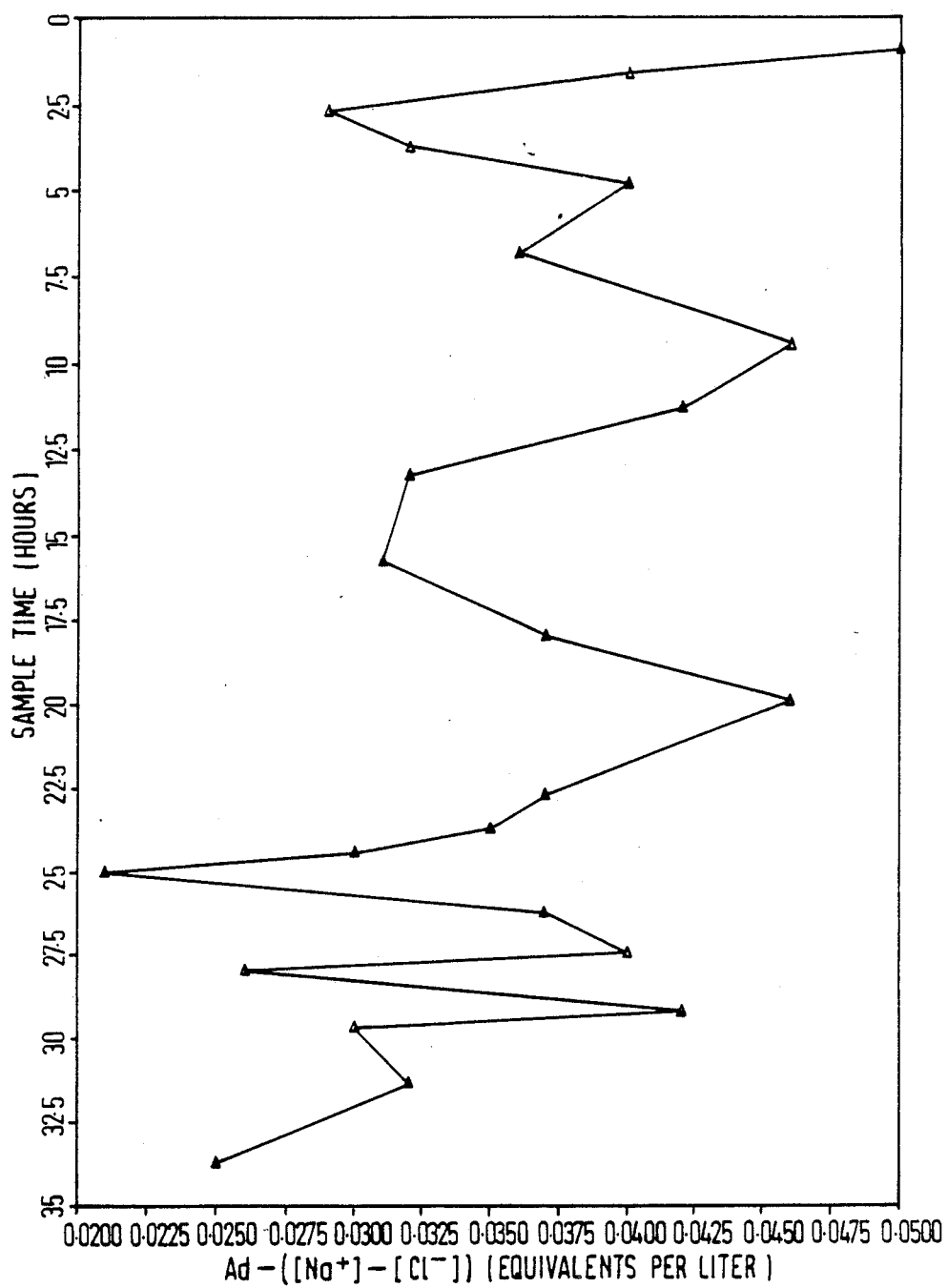
FIGS. 24 and 25 show the apparent anion deficit (Ad) minus (Sodium-chloride) concentrations (equivalents per litre) versus the sample time (in hours) and the magnesium concentration (equivalents per litre), respectively.
Figure 25:
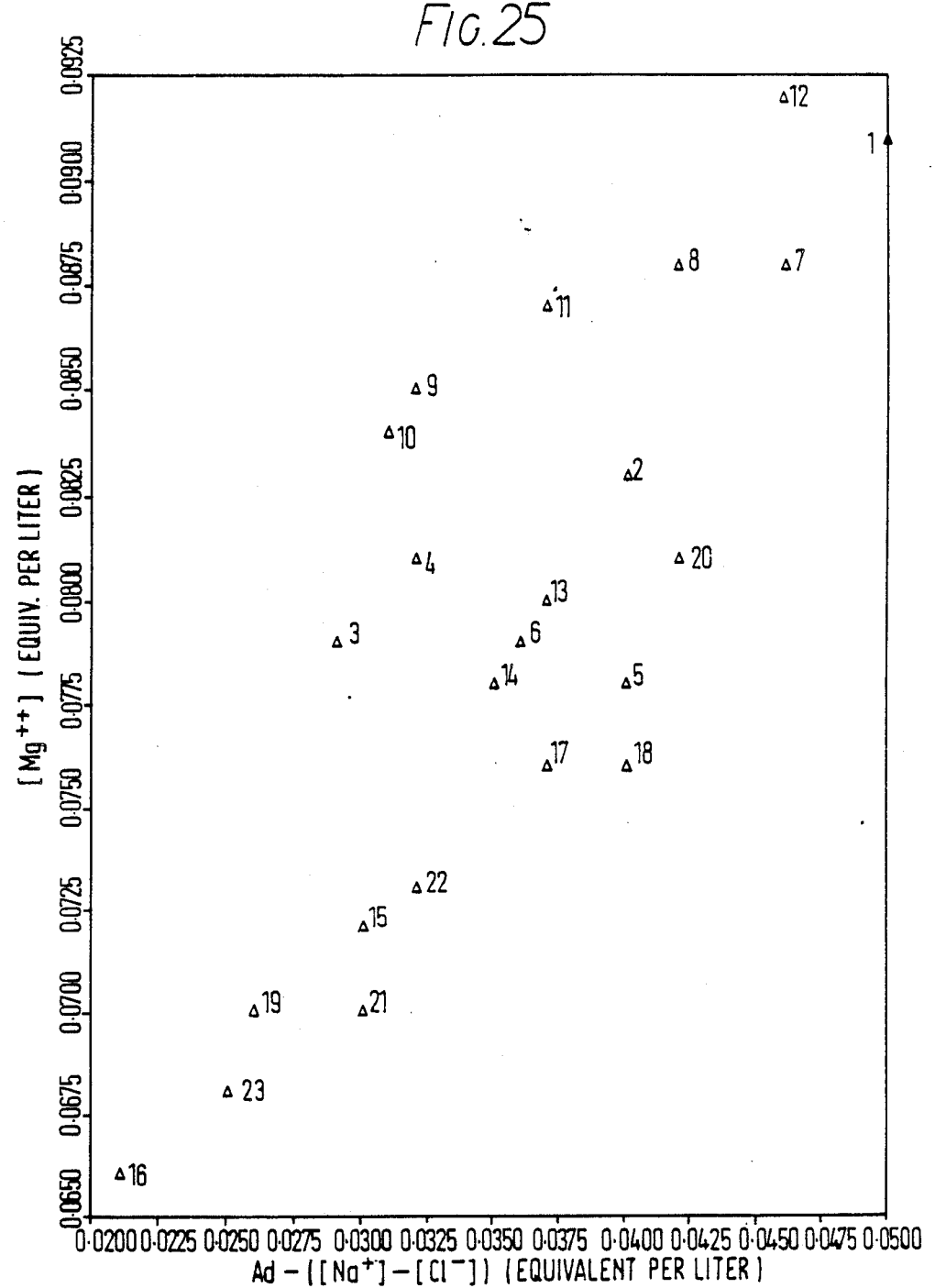

FIG. 24 represents the variation of Ad-([Na]-[Cl]) with sample time, and shows a good correlation with both the magnesium and calcium ion concentrations (FIGS. 18 and 19, respectively). The second source of carbonate in the mud filtrate samples appears to be calcium and magnesium carbonates which are obtained from the drilled formations. The cross-plot of [Mg] as a function of Ad-([Na]-[Cl]), FIG. 25, shows linear behavior with a gradient of unity, although the [Mg] expressed as equivalents per litre is significantly bigger than Ad-([Na]-[Cl]) and therefore not all of the magnesium present occurs as magnesium carbonate. The general trend of the data is that the first and second formations (points 1-9) are characterized by high magnesium and high carbonate values, while the third, fourth and fifth formations occur at lower values of magnesium and carbonate.

Figure 26:
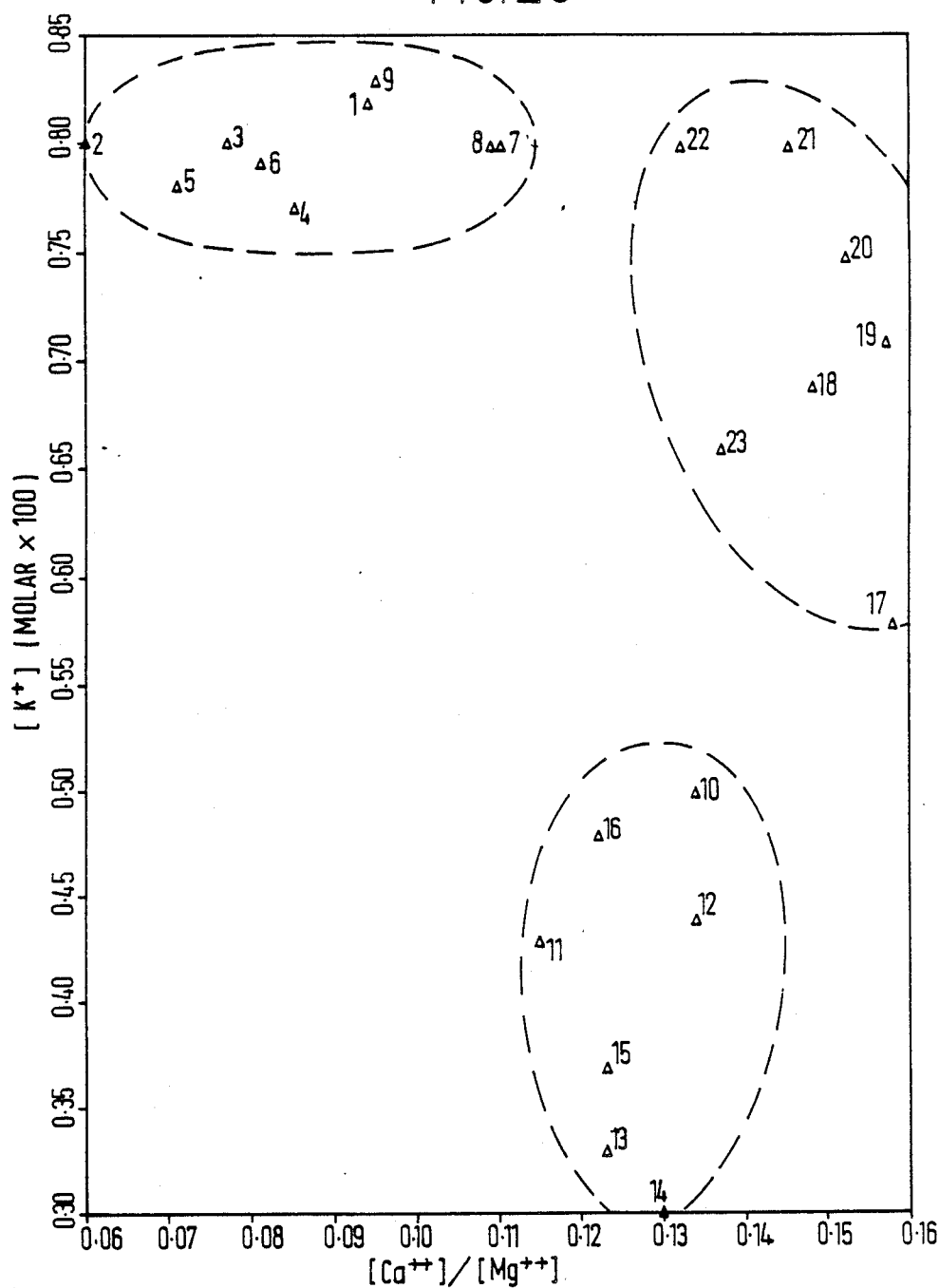
FIG. 26 shows the calcium/magnesium ratio of filtrate samples versus the potassium concentration (molar × 100).

The measured chemical (ionic) composition of the mud filtrate samples has shown that a reasonable relationship exists between filtrate composition and drilled lithology. It appears that the only measured mud-formation interaction is that between the mud and the cuttings, which implies that once a formation is drilled, the only significant contribution that it makes to mud composition is by the continual addition of solids, eg, cavings. Different types of formations can be distinguished by the magnesium and calcium content of the filtrates, some being characterized by a high Ca/Mg ratio while other formations exhibit lower Ca/Mg ratios. The potassium content of the filtrate samples also showed good contrast between the shale and non-shale formations. FIG. 26 shows a cross-plot of the potassium concentration as a function of the calcium:magnesium ratio. The first and second formations (points 1-9) are well separated from the third, fourth and fifth formations (points 10-16) both vertically by the potassium content and horizontally by Ca/Mg.

The lower points, 17-23, lie at higher potassium and Ca/Mg values than the upper ones (points 10-16) and appear to be approaching the value of the potassium concentration ($0.99 \times 10^{-2}$ molar) and Ca/Mg ratio (0.196) in seawater. Points 17-23 can be ascribed to dilution of the mud system by seawater in a formation, and are still quite distinct from the composition of the filtrate in the first and second formations. The ordering of points 17-23 in FIG. 28 suggests that the dilution of the mud system had stopped by the time sample 22 was taken, and that the composition of filtrate sample 23 is approaching characteristic values of potassium and Ca/Mg for the shale points 10-16.

Another important and similar graph (not illustrated here), leading to about the same results consists in cross-plotting the potassium/sodium ion concentration ratio and the Ca/Mg ion concentration ratio.

The initial analysis of the data shown in FIG. 26 illustrates a major problem encountered in the interpretation of any chemical mud logging measurements, namely, the distinction between additions to the mud system at the surface and downhole processes such as ion exchange and formation water influxes. In general it will not be possible to isolate borehole processes using only the measurement of mud composition in the active tank, unless there is a detailed knowledge of all additions.

The best solution to the problem of processes discrimination is to sample from both the active tank and the return mud flow at the shale shaker. These two measurements of composition allow additions to the mud system at the surface to be measured by comparison of return and active mud samples at the same time (assuming the travel time from shaker to active tank is negligible in comparison to round trip time) and the direct measurement of borehole processes by following an element of mud around the borehole from active tank to shaker over the duration of the round trip time. The return mud stream was sampled at the same time as the active tank and a direct comparison can therefore be made.

The above analysis has shown that there is a good correlation between drilled lithology and mud filtrate composition. In particular, the non-shale formations are associated with mud filtrates with a high potassium content and a low Mg/Ca ratio, while the shale formations are generally associated with a low potassium concentration and high Mg/Ca ratio. The non-shale formations are also associated with generally higher carbonate/bicarbonate concentrations. The sharp decrease in the potassium ion concentration gave good resolution to the non-shale/shale bed boundary, while the magnesium ion concentration gave a good indication of the transition from one shale bed to the next shale bed. The discrimination of lithology from the chemical composition of mud filtrate samples implies that the drilled cuttings are the major contributor to the change in composition.

Analysis of the change in chemical composition of the mud from the active tank alone does not allow full discrimination between additions to the mud at surface and downhole processes. The active mud analysis must be compared with the corresponding analysis of the return mud flow. The erratic variation of active mud composition measured in the latter stages of sampling suggests local concentrations due to mixing in the active tank.

The analysis has also shown that considerable quantities of sodium chloride appeared to be added to the mud system, largely as impurities in the mud products, particularly CMC. The addition of sodium chloride was accompanied by a considerable build up of carbonate (strictly the anion deficit) in the mud system, partly from sodium carbonate (added as a mud product or as a contaminant in the bentonite) and partly from the drilled formations. The anion deficit has the third largest concentration of any ion species after sodium and chloride. It has also been noticed that, when the mud does not circulate (due for example to the temporary stop of the drilling) and the well stays inactive for a while (at least a few hours), the same portions of the mud in the borehole remain in contact with the respective formations traversed by the borehole. Ion exchanges between the mud and the formations then occur. When the circulation of the mud resumes and the mud is sampled again at the surface, the chemical analysis of the samples have shown that each portion of the mud, which stayed for a while in contact with the same underground formation, had chemical characteristics (ion concentrations, pH and/or CEC) specific to said formation. It is therefore possible, according to the present invention, to determine the formations traversed by the borehole and their properties by sampling the mud and analyzing its chemical characteristics, each sample corresponding to a certain depth and therefore to a certain formation, until the whole column of mud in the borehole has been circulated up to the surface and analyzed.

We claim:

1. In a method of testing drilling mud circulating in a borehole being drilled with a drilling rig, the chemical composition of said mud for an on-going drilling operation being specified within certain desired limits, wherein the improvement comprises periodically taking samples of the circulating mud and separating out aqueous filtrates, analyzing the aqueous filtrates on site by ion chromatography for determining selected positive and negative ion concentrations and determining if the chemical composition of the mud is within said desired limits.

2. A method according to claim 1 wherein the aqueous filtrate is analyzed for at least two of the group consisting of sodium, potassium, calcium, chloride and sulphate ions.

3. A method according to claim 1 wherein the ionic composition of a mud sample is assessed by ascertaining the volume fraction of aqueous filtrate in the mud, measuring the concentration of an ion or ions in the aqueous filtrate, and calculating the concentration of said ion in the mud from this volume fraction and the measured concentration of said ion in the aqueous filtrate.

4. A method according to claim 1 including monitoring the concentration of an ion in consecutive mud samples and comparing its concentration with the concentration of said ion in a reference sample, and ascertaining therefrom whether the mud is out of specification or estimating therefrom when it will move out of specification.

5. A method according to claim 1 wherein hydrodynamic dispersion effects on the ionic concentration of the circulating mud is ascertained by including in the mud at least one tracer ion substantially inert to borehole reactions, taking mud samples periodically an separating out the aqueous filtrates and analyzing the mud sample filtrates for said tracer ion by ion chromatography to monitor changes of tracer ion concentration in the mud.

6. A method according to claim 1 including detecting calcium and magnesium ion concentrations, cross-plotting the calcium and magnesium ion concentrations of the samples and detecting from the cross-plot changes as drilling proceeds.

7. A method according to claim 1 including detecting the potassium ion concentration or the potassium/sodium ion concentration ratio, detecting the calcium/magnesium ion concentration ratio, cross-plotting the potassium ion concentration or the potassium/sodium ion concentration ratio and the calcium/magnesium ion concentration ratio of the samples and detecting from the cross-plot changes as drilling proceeds.

8. A method according to claim 1 including adjusting the composition of the mud, according to the determined selected positive and negative ion concentrations, towards the desired limits of the chemical composition of the mud as drilling proceeds.

9. A method according to claim 1 which includes analyzing samples taken substantially simultaneously from the mud entering the borehole and the mud flowing out of the borehole and comparing the analyses to discriminate between additions of components to the mud by surface and downhole processes.

10. A method according to claim 1 further including measuring the pH of each sample concurrently with the determination of its chemical composition.

11. A method according to claim 1 or 10 further including measuring the temperature of each sample concurrently with the determination of its chemical composition.

12. A method according to claim 1 wherein each sample is taken from a specified location in the circulating mud at a known time, and the anion, monovalent cation and divalent cation contents of the aqueous filtrate of the sample are determined.

13. A method according to claim 12, wherein the anion, monovalent cation and divalent cation contents of the aqueous filtrate of the sample are determined by three separate ion chromatography units.

14. A method according to claim 1 including ascertaining any apparent anion charge deficit of a sample to indicate the concentration of anion(s) not provided by ion chromatography and pH measurement.

15. A method according to claim 14 wherein the concentration of an unanalyzed anion contributing to any apparent anion charge deficit is ascertained by reference to a database of equilibrium constants over ranges of pH and temperature for reactions relevant to the mud and involving hydroxide, carbonate and bicarbonate ions and relevant cations, measuring the pH and temperature of the sample, when said step of measuring the concentration of selected anions includes all such anions which can be measured by ion chromatography and deriving therefrom the concentration of the unanalyzed anion at the measured pH and temperature of the sample and at the measured concentration of the other ions in the sample.

16. A method according to claim 1 in which solids contained in the sample of mud are separated out and analyzed on site for sorbed ions either directly or together with the residual cation exchange capacity of said mud solids.

17. A method according to claim 16 wherein the solids of a mud sample are dried and then washed free of sorbed ions, a known weight of the washed solids is ion exchanged with a replacement cation, in a known volume of a solution resulting from the wash of the dried solids, the resulting solution containing ions released from the solids is analyzed by ion chromatography to identify the cations and to determine their concentrations, the measured total concentration of cations released is normalized to dry solid weight and the cation exchange capacity of the mud solids is determined.

18. A method according to claim 16 wherein the solids of a mud sample are dried, a known weight of the dried solids is washed to remove sorbed ions, and cation(s) and anion(s) in a solution resulting from the wash of the dried solids are identified and assayed by ion chromatography.

19. A method according to claim 18 wherein a known weight of the washed solids is ion exchanged with a replacement cation, in a known volume of the solution resulting from the wash of the dried solids, the solution is analyzed by ion chromatography before and after ion exchange, a decrease in replacement ion concentration in the solution is ascertained and normalized to dry solid weight and the cation exchange capacity of the mud solids is determined.

20. A method of analyzing drilled cuttings in a drilling mud circulating in a borehole being drilled, comprising separating the cuttings from the mud, drying the cuttings, washing a known weight of the dried cuttings in a known volume of solvent to place the sorbed ions into solution and analyzing the solution by ion chromatography for selected positive and negative ions.

21. A method of analyzing drilled cuttings in a drilling mud circulating in a borehole being drilled, comprising separating the cuttings from the mud, drying the cuttings, washing them to remove the sorbed ions, mixing a known weight of the washed cuttings with a known volume of solution so as to release into the solution the remaining ions still present in the cuttings, analyzing by ion chromatography at least the cation content of the solution, and determining the cation exchange capacity.

22. A method of analyzing drilled cuttings in a drilling mud wherein the drilled cuttings are dried and then washed free of sorbed ions, a known weight of the washed cuttings is ion exchanged with a replacement cation, in a known volume of solution, the resulting solution containing ions released from the cuttings is analyzed by ion chromatography to identify the cations and measure their concentrations, the total concentration of cations released is calculated from the measured concentrations and then normalized to the dry cuttings weight, and the cation exchange capacity of the drilled cuttings is determined.

23. A method of analyzing drilled cuttings in a drilling mud wherein the drilled cuttings are dried and then washed free of sorbed ions, a known weight of the washed cuttings is ion exchanged with a replacement cation, in a known volume of solution, the solution is analyzed by ion chromatography before and after ion exchange, the decrease in replacement ion concentration in the solution is ascertained and normalized to dry cuttings weight, and the cation exchange capacity of the drilled cuttings is determined.

24. A method according to one of claims 17, 19, 22, or 23 further including cross-plotting the cation exchange capacity and an indication of the content of thorium and potassium in the drilled formation so as to produce a 3 dimensional cross-plot and to characterize the formation from said cross-plot.

25. A method of testing drilling mud circulating in a borehole being drilled with a drilling rig, which comprises periodically sampling the circulating mud, separating out an aqueous filtrate, analyzing the aqueous filtrate on site by ion chromatography for determining selected positive and negative ion concentrations, storing the ion concentration data and comparing them with already stored data.

26. A method according to claim 25 wherein the already stored data are data previously acquired by analysis of preceding mud filtrate samples.

27. A method according to claim 25 wherein a formulation of the mud for drilling the borehole, or part of it, is specified, the already stored data are reference data characteristic of the specified mud formation and the mud composition is adjusted to return to the specified mud formation.

28. A method according to claim 25 including cross-plotting calcium and magnesium ion concentrations of the samples and detecting, from the cross-plot, changes in mud characteristics as drilling proceeds.

29. A method according to claim 25 including cross-plotting the potassium ion concentration or the potassium/sodium ion concentration ratio and the calcium/magnesium ion concentration ratio of the samples and detecting from the cross-plot changes as drilling proceeds.

30. A method according to claim 25 including analyzing drilled cuttings from the drilling mud, storing the data resulting from the analysis and monitoring the changes in the data from preceding analyses.

31. A method according to claim 30 wherein the drilled cuttings are analyzed for determining at least one of the group consisting of cation exchange capacity, pore water salt, water content and exchange cations.

32. In a method analyzing drilled cuttings in a drilling mud circulating in a borehole being drilled, wherein the improvement comprises separating the cuttings from the mud, drying the cuttings, extracting ions from a known weight of the separated dried cuttings into a known volume of a solution containing a salt of a replacement cation, analyzing the resulting solution by ion chromatography, determining total concentrations of cations and anions released from the cuttings into the solution and determining the cation exchange capacity of the drilled cuttings from the difference between the total cation and anion concentrations.

* * * * *